(12) United States Patent
Inaba et al.

(10) Patent No.: US 6,336,997 B1
(45) Date of Patent: Jan. 8, 2002

(54) PROCESS FOR REFINING HEAT-DETERIORATIVE COMPOUND, CONTAINED IN MULTI-COMPONENT LIQUID MIXTURE, BY DISTILLATION

(75) Inventors: Yukio Inaba; Kazunori Fujita; Hiroshi Kofuji, all of Ube (JP)

(73) Assignee: Ube Industries, Ltd., Ube (JP)

( * ) Notice: Subject to any disclaimer, the term of this patent is extended or adjusted under 35 U.S.C. 154(b) by 0 days.

(21) Appl. No.: 09/241,557

(22) Filed: Feb. 1, 1999

(30) Foreign Application Priority Data

Jan. 30, 1998 (JP) .......................................... 10-019062
Mar. 13, 1998 (JP) .......................................... 10-062375

(51) Int. Cl.⁷ .............................. B01D 3/28; B01D 3/42
(52) U.S. Cl. .............................. 203/1; 159/49; 203/72; 203/84; 203/89; 203/98; 203/DIG. 9
(58) Field of Search .............................. 203/72, 73, 78, 203/80, 89, 84, DIG. 9, 1, 3, 98; 202/236, 172; 159/49; 568/752, 753, 913; 585/800; 560/79, 218; 562/405

(56) References Cited

U.S. PATENT DOCUMENTS

| | | | | |
|---|---|---|---|---|
| 3,634,200 A | * | 1/1972 | Obrecht et al. ............... | 203/72 |
| 3,893,893 A | * | 7/1975 | Miserlis et al. .............. | 202/174 |
| 4,308,112 A | * | 12/1981 | Vupe et al. ................... | 203/80 |
| 4,394,221 A | * | 7/1983 | Stage et al. ................... | 203/89 |
| 4,566,947 A | * | 1/1986 | Tsuruta ........................ | 203/83 |
| 4,683,025 A | | 7/1987 | Flores | |
| 5,582,692 A | * | 12/1996 | Baird ........................... | 203/49 |
| 5,670,028 A | * | 9/1997 | Inaba et al. ................... | 203/86 |

FOREIGN PATENT DOCUMENTS

| | | | |
|---|---|---|---|
| EP | 0460917 | | 12/1991 |
| WO | 31445 | * | 7/1998 |

OTHER PUBLICATIONS

European Search Report corresponding to 0460917.

* cited by examiner

Primary Examiner—Virginia Manoharan
(74) Attorney, Agent, or Firm—Morgan, Lewis & Bockius LLP

(57) ABSTRACT

A heat-deteriorative compound contained in a liquid mixture is refined by a distillation procedure using a distillation column in which a vapor fraction and a liquid fraction containing the heat-deteriorative compound are generated from the liquid mixture, and a liquid film-falling reboiler in which the liquid fraction falls in the form of liquid films along inner surfaces of a plurality of vertical heat-conductive pipes at a Reynolds number (Re) of 700 to 10,000 and heated to a temperature lower than the heat-deterioration temperature of the heat deteriorative compound to such an extent that 1 to 15% by weight of the liquid fraction is evaporated per pass through the reboiler, the heated liquid fraction being returned into the distillation column to generate the vapor fraction from the liquid mixture fed into the distillation column.

18 Claims, 3 Drawing Sheets

PROCESS FOR REFINING HEAT-DETERIORATIVE COMPOUND, CONTAINED IN MULTI-COMPONENT LIQUID MIXTURE, BY DISTILLATION

BACKGROUND OF THE INVENTION

1. Field of the Invention

The present invention relates to a process for refining a heat deteriorative compound, contained in a multi-component liquid mixture, by distillation. More particularly, the present invention relates to a process for refining a heat deteriorative compound, for example, hydroquinone or catechol which are consumed by thermal decomposition, thermal modification or thermal polymerization when heated, and contained in a multi-component liquid mixture, by a specific distillation procedure by which the multi-component liquid mixture is separated, at a temperature lower than the heat deterioration-starting temperature of the heat-deteriorative compound, into a liquid fraction containing a higher boiling temperature component including the heat-deteriorative compound and a vapor fraction containing a lower boiling temperature component which is substantially free from the heat-deteriorative compound and is removed from the multi-component liquid mixture.

2. Description of the Related Art

It is known that a reduced pressure (vacuum) distillation apparatus equipped with a liquid film-falling reboiler attached to a distillation column is advantageous in that the liquid mixture can be distilled even under a reduced pressure, while keeping the temperature of a liquid fraction accumulated in a bottom portion of the distillation column at a relatively low level, and is thus widely utilized for various distillations which must be carried out at a relatively low distillation temperature.

When the conventional distillation apparatus comprising a distillation column, which may be a reduced pressure distillation column and a liquid film-falling reboiler attached to the distillation column, is used to distil, optionally under a reduced pressure, a liquid mixture containing a heat-deteriorative compound, and a liquid fraction generated in the distillation column is fed into the reboiler and falls in the form of liquid films through a plurality of heat-conductive pipes of the reboiler, such a disadvantageous phenomenon that the falling liquid films are broken on portions of the inner surfaces of the heat conductive pipes, and thus the portions of the inner surfaces of the heat conductive pipes are directly exposed to the air atmosphere without being covered by the falling liquid film of the liquid fraction, may occur. When the phenomenon occurs, the portions of the inner surfaces not covered by the falling liquid films are locally over-heated to a higher temperature than the temperature of the other portions of the inner surfaces, and thus portions of the falling liquid films located in boundaries between the liquid film-covered portions and non-covered portions of the inner surfaces of the heat conductive pipes are also locally overheated to a higher temperature than that of the other portions. Accordingly, the heat-deteriorative compound contained in the locally over-heated portions of the falling liquid films is thermally deteriorated to a great extent. Therefore, the heat deteriorative compound contained in the liquid mixture is converted to a high boiling temperature substance (for example, polymer), a thermally decomposed product or a thermally modified product, and consumed in a high proportion during the distillation procedure in the reboiler. In a certain case in which the resultant high boiling temperature substance, for example, a polymeric substance, deposits on and adheres to the inner surfaces of the heat conductive pipes, to form scale, the resultant scale causes the falling of the liquid film along the inner surfaces of the heat conductive pipes to be obstructed and finally stopped, and thus the distilling procedure must be stopped after a short time.

For example, in a conventional process for producing an alkyl ether of an aromatic dihydroxyl compound by an etherifying reaction of an aromatic dihydroxyl compound, for example, hydroquinone or catechol with a lower alkyl alcohol, for example, methyl alcohol or ethyl alcohol, the reaction product liquid comprising a lower boiling temperature component containing the non-reacted lower alkyl alcohol and a higher boiling temperature component containing the non-reacted aromatic dihydroxyl compound and the resultant alkyl ether of the aromatic dihydroxyl compound is distilled by a conventional distillation procedure at a high temperature to collect the target reaction product and to recover the non-reacted compounds. In this conventional distillation procedure, the aromatic dihydroxyl compound which exhibits a high thermal deterioration property is concentrated and thermally deteriorated at the high temperature. The thermal deterioration results in a disadvantageous consumption or loss of the aromatic dihydroxyl compound. Also, in a certain case, the heat-deterioration product deposits and adheres to an inner surface of a heater (or reboiler) of the distillation apparatus and the continuous distilling procedure over a long time is obstructed.

Namely, in the process for producing the alkyl ether of the aromatic dihydroxyl compound, no specific method of refining the target aromatic dihydroxyl compound and of recovering the non-reacted lower alkyl alcohol and aromatic dihydorxyl compound, without heat deterioration of the aromatic dihydroxyl compound has yet been concretely provided.

As mentioned above, the reduced pressure (vacuum) distillation apparatus including the liquid film-falling reboiler attached to a distillation column is advantageous in that the liquid fraction accumulated in the bottom portion of the distillation column can be distilled even under a reduced pressure without a need of heating to a high temperature. Therefore, the reduced pressure distillation apparatus can be used for a distillation procedure for a liquid mixture containing the alkyl ether of aromatic dihydroxyl compound produced by the reaction of the alkyl alcohol with the aromatic dihydroxyl compound.

However, when the distillation procedure is carried out under conventional conditions, the liquid films falling along the inner surfaces of the heat conductive pipes of the reboiler are frequently broken and thus the heat-deteriorative compound contained in the liquid film is thermally deteriorated as mentioned hereinbefore. No specific means for preventing the breakage of the falling liquid films on the inner surfaces of the heat conductive pipes of the reboiler has been known.

SUMMARY OF THE INVENTION

An object of the present invention is to provide a process for refining a heat-deteriorative compound contained in a multi-component liquid mixture by using a distillation column and a liquid film falling reboiler attached to the distillation column and having a plurality of vertical heat-conductive pipes through which a liquid fraction generated from the liquid mixture in the distillation column and containing the heat-deteriorative compound falls in the form of liquid films along the inner surface of the vertical pipes while being heated and evaporated, in which process, local breakages of the liquid films on the inner surface of the vertical pipes can be prevented, to protect the heat-deteriorative compound in the liquid fraction from heat-deterioration in the reboiler, and thus the heat-deteriorative compound contained in the liquid mixture can be continuously concentrated and refined with a high stability and with a high yield over a long time period.

The above-mentioned object can be attained by the process of the present invention for refining a heat-deteriorative compound, contained in a multi-component liquid mixture, by distillation, which comprises the steps of:

(1) feeding a multi-component liquid mixture comprising a lower boiling temperature component and a higher boiling temperature component containing a heat-deteriorative compound, into a distillation column having a top outlet located in a top portion of the distillation column and a bottom outlet located in a bottom portion of the distillation column, the bottom outlet being connected to a liquid film-failing reboiler having a plurality of heat-conductive vertical pipes spaced from each other and arranged in a heating chamber through which a heating medium passes:

(2) distilling the multi-component liquid mixture in the distillation column to generate a vapor fraction comprising the lower boiling temperature component and a liquid fraction comprising the higher boiling temperature component, in such a manner that (A) the liquid fraction is withdrawn through the bottom outlet of the distillation column and introduced into the reboiler to allow the introduced liquid fraction to fall in the form of films along inner surfaces of the vertical pipes; (B) the falling liquid fraction through the vertical pipes is heated by the heating medium passing through the heating chamber at a temperature lower than the heat-deterioration-starting temperature of the heat-deteriorative compound but sufficient to evaporate the liquid fraction, to evaporate a portion of the falling liquid fraction in an evaporation amount in kg/hr corresponding to 1 to 15% by weight of the total amount in kg/hr of the liquid fraction introduced into the reboiler, per one pass of the liquid fraction through the reboiler; (C) the resultant evaporated and non-evaporated portions of the liquid fraction are withdrawn from the reboiler and returned into the distillation column through a returning inlet thereof located above the level of the liquid fraction accumulated in the bottom portion of the distillation column; and (D) the evaporated portion of the returned liquid fraction heat-exchanges to the multi-component liquid mixture fed into the distillation column to evaporate the lower boiling temperature component;

(3) delivering the resultant vapor fraction comprising the lower boiling temperature component through the top outlet of the distillation column, while allowing the resultant liquid fraction comprising the higher boiling temperature component to be accumulated in the bottom portion of the distillation column; and (4) recovering a portion of the liquid fraction accumulated in the bottom portion of the distillation column and comprising the higher boiling temperature component containing the heat-deteriorative compound from the bottom portion of the distillation column.

When the higher boiling temperature component contained in the liquid fraction recovered in the recovery step (4) contains, in addition to the heat-deteriorative compound, at least one organic compound having a boiling temperature lower than that of the heat-deteriorative compound, the process of the present invention further comprises the steps of:

(5) feeding the recovered liquid fraction into an additional distillation column having a top outlet located in a top portion of the additional distillation column and a bottom outlet located in a bottom portion of the additional distillation column, the bottom outlet being connected to an additional liquid film-falling reboiler having a plurality of heat-conductive vertical pipes spaced from each other and arranged in a heating chamber through which a heating medium passes;

(6) distilling the fed liquid fraction in the additional distillation column to generate a liquid fraction comprising the heat-deteriorative compound and a vapor fraction comprising the organic compound having a lower boiling temperature than that of the heat-deteriorative compound, in such a manner that (E) the liquid fraction is withdrawn through the bottom outlet of the additional distillation column and introduced into the additional reboiler to allow the introduced liquid fraction to fall in the form of films along inner surfaces of the vertical pipes of the additional reboiler; (F) the falling liquid fraction through the vertical pipes is heated by the heating medium passing through the heating chamber at a temperature lower than the heat deterioration-starting temperature of the heat-deteriorative compound but sufficient to evaporate the falling liquid fraction, to evaporate a portion of the falling liquid fraction in an evaporation amount in kg/hr corresponding to 1 to 15% by weight of the total amount in kg/hr of the liquid fraction introduced into the additional reboiler, per one pass of the liquid fraction through the additional reboiler; (G) the resultant evaporated and non-evaporated portions of the liquid fraction are withdrawn from the additional reboiler and returned into the additional distillation column through a returning inlet thereof located above the level of the liquid fraction accumulated in the bottom portion of the additional distillation column; and (H) the returned evaporated portion in the additional distillation column heat-exchanges to the recovered liquid fraction fed into the additional distillation column, to evaporate the organic compound having the lower boiling temperature than that of the heat-deteriorative compound;

(7) delivering the resultant vapor fraction comprising the organic compound having the lower boiling temperature than that of the heat-deteriorative compound through the top outlet of the additional distillation column, while allowing the resultant liquid fraction comprising the heat-deteriorative compound to be accumulated in the bottom portion of the additional distillation column; and (8) recovering a portion of the liquid fraction, accumulated in the bottom portion of the additional distillation column and comprising the heat-deteriorative compound, through the bottom outlet of the additional distillation column.

Further, when the liquid fraction recovered from the additional distillation column in step (8) contains, in addition to the heat-deteriorative compound, at least one organic compound having a higher boiling temperature than that of the heat-deteriorative compound, the process of the present invention further comprising the steps of:

(9) feeding the recovered liquid fraction from the additional distillation column into a further additional distillation column having a top outlet located in a top portion of the further additional distillation column and a bottom outlet located in a bottom portion of the further additional distillation column, the bottom outlet being connected to a further additional liquid film-falling reboiler having a plurality of heat conductive vertical pipes spaced from each other and arranged in a heating chamber through which a heating medium passes;

(10) distilling the fed liquid fraction in the further additional distillation column to generate a vapor fraction comprising the heat-deteriorative compound and a liquid fraction comprising the organic compound having the higher boiling temperature than that of the heat-deteriorative compound, in such a manner that (I) the liquid fraction in the further additional distillation column is withdrawn through the bottom outlet of the further additional distillation column and introduced into the further additional reboiler to allow the introduced liquid fraction to fall in the form of films along inner surfaces of the vertical pipes of the further additional reboiler; (J) the falling liquid fraction through the vertical pipes is heated by the heating medium, passing through the heating chamber, at a temperature lower than the heat-deterioration-starting temperature of the heat-deteriorative compound but sufficient to evaporate the falling liquid fraction, to evaporate a portion of the failing liquid fraction in an evaporation amount in kg/hr corresponding to 1 to 15% by weight of the total amount in kg/hr of the liquid fraction introduced into the further additional reboiler, per one pass of the liquid fraction through the further additional reboiler; (K) the resultant evaporated and non-evaporated portions of the liquid fraction are withdrawn from the further additional reboiler and are returned into the further additional distillation column through a returning inlet thereof located above the level of the liquid fraction accumulated in the bottom portion of the further additional distillation column; and (L) the returned evaporated portion in the further additional distillation column heat-exchanges to the recovered liquid fraction into the further additional distillation column, to evaporate the heat-deteriorative compound;

(11) recovering the resultant vapor containing the heat-deteriorative compound through the top outlet of the further additional distillation column, while allowing the resultant liquid fraction comprising the organic compound having higher boiling temperature than that of the heat-deteriorative compound to be accumulated in the bottom portion of the further additional distillation column; and

(12) discharging a portion of the liquid fraction accumulated in the bottom portion through the bottom outlet of the further additional distillation column.

In an embodiment of the process of the present invention, (1) a multi-component liquid mixture comprising a lower boiling temperature component comprising at least one alkyl alcohol having 1 to 20 carbon atoms and a higher boiling temperature component comprising a heat-deteriorative aromatic compound having two or more hydroxyl groups and at least one alkyl ether of the aromatic compound having two or more hydroxyl groups, is fed into a first distillation column having a top outlet located in a top portion of the first distillation column and a bottom outlet located a bottom portion of the first distillation column, the bottom outlet being connected to a first liquid film-falling reboiler having a plurality of heat-conductive vertical pipes spaced from each other and arranged in a heating chamber through which a heating medium passes;

(2) the fed multi-component liquid mixture is distilled in the first distillation column to generate a vapor fraction comprising the lower boiling temperature component and a liquid fraction comprising the higher boiling temperature component, in such a manner that (A) the liquid fraction is withdrawn through the bottom outlet of the first distillation column and introduced into the first reboiler in which the introduced liquid fraction falls in the form of films along the inner surfaces of the vertical pipes; (B) the falling liquid fraction is heated by the heating medium passing through the heating chamber at a temperature lower than the heat-deterioration-starting temperature of the aromatic compound having two or more hydroxyl groups but sufficient to evaporate the falling liquid fraction, to evaporate a portion of the falling liquid fraction in an evaporation amount in kg/hr corresponding to 1 to 15% by weight of the total amount in kg/hr of the liquid fraction introduced into the first reboiler, per one pass of the liquid fraction through the first reboiler; (C) the resultant evaporated and non-evaporated portions of the liquid fraction are withdrawn from the first reboiler and returned into the first distillation column through a returning inlet thereof located above the level of the liquid fraction accumulated in the bottom portion of the first distillation column; and (D) the evaporated portion of the returned liquid fraction heat-exchanges with the multi-component liquid mixture fed into the first distillation column to evaporate the lower boiling temperature component;

(3) the resultant vapor fraction comprising the lower boiling temperature component is delivered through the top outlet of the first distillation column, while allowing the resultant liquid fraction comprising the higher boiling temperature component to accumulate in the bottom portion of the first distillation column;

(4) a potion of the liquid fraction accumulated in the bottom portion of the first distillation column and comprising the higher boiling temperature component containing the heat-deteriorative aromatic di- or more hydroxyl compound is recovered through the bottom outlet of the first distillation column;

(5) the recovered liquid fraction, which comprises the higher boiling temperature component comprising the heat-deteriorative aromatic di- or more hydroxyl compound and the alkylether of the heat-deteriorative aromatic compound having a boiling temperature lower than that of the heat-deteriorative compound, is fed into a second distillation column having a top outlet located in a top portion of the second distillation column and a bottom outlet located in a bottom portion of the second distillation column, the bottom outlet being connected to a second liquid film-falling reboiler having a plurality of heat-conductive vertical pipes spaced from each other and arranged in a heating chamber through which a heating medium passes;

(6) the fed liquid fraction is distilled in the second distillation column to generate a liquid fraction comprising the heat-deteriorative aromatic compound and a vapor fraction comprising the alkylether of the heat-deteriorative aromatic compound having a lower boiling temperature than that of the heat-deteriorative aromatic compound, in such a manner that (E) the liquid fraction in the second distillation column is withdrawn through the bottom outlet of the second distillation column and introduced into the second reboiler to allow the introduced liquid fraction to fall in the form of liquid films along inner surfaces of the vertical pipes of the second reboiler; (F) the liquid fraction falling through the vertical pipes is heated by the heating medium passing through the heating chamber at a temperature lower than the heat-deterioration-starting temperature of the heat-deteriorative aromatic compound but sufficient to evaporate the falling liquid fraction, to evaporate a portion of the falling liquid fraction in an evaporation amount in kg/hr corresponding to 1 to 15% by weight of the total amount in kg/hr of the liquid fraction introduced into the second reboiler, per one pass of the liquid fraction through the second reboiler; (G) the resultant evaporated and non-evaporated portions of the liquid fraction are withdrawn from the second reboiler and returned into the second distillation column through a returning inlet thereof located above the level of the liquid fraction accumulated in the bottom portion of the second distillation column; and (H) the returned evaporated portion in the second distillation column heat-exchanges to the recovered liquid fraction fed into the second distillation column, to evaporate the alkylether of the heat-deteriorative aromatic compound having the lower boiling temperature than that of the heat-deteriorative compound;

(7) the resultant vapor fraction comprising the alkylether of the heat-deteriorative aromatic compound having the lower boiling temperature than that of the heat-deteriorative aromatic compound is delivered through the top outlet of the second distillation column, while allowing the resultant liquid fraction comprising the heat-deteriorative compound to be accumulated in the bottom portion of the second distillation column; and (8) a portion of the liquid fraction accumulated in the bottom portion of the second distillation column and comprising the heat-deteriorative aromatic compound is recovered through the bottom outlet of the second distillation column.

In the embodiment of the present invention, when the liquid fraction recovered from the second distillation column contains, in addition to the heat-deteriorative compound, at least one organic compound having a higher boiling temperature than that of the heat-deteriorative aromatic compound, the recovered liquid fraction is further refined by the procedure in which;

(9) the recovered liquid fraction from the second distillation column is fed into a third distillation column having a top outlet located in a top portion of the third distillation column and a bottom outlet located in a bottom portion of the third distillation column, the bottom outlet being connected to a third liquid film-falling reboiler having a plurality of heat-conductive vertical pipes spaced from each other and arranged in a heating chamber through which a heating medium passes;

(10) the fed liquid fraction is distilled in the third distillation column to generate a vapor fraction comprising the heat-deteriorative compound and a liquid fraction comprising the organic compound having the higher boiling temperature than that of the heat-deteriorative compound, in such a manner that (I) the liquid fraction in the third distillation column is withdrawn through the bottom outlet of the third distillation column and introduced into the third reboiler to allow the introduced liquid fraction to fall in the form of films along inner surfaces of the vertical pipes of the third reboiler; (J) the falling liquid fraction through the vertical pipes is heated by the heating medium passing through the heating chamber at a temperature lower than the heat-deterioration-starting temperature of the heat-deteriorative compound but sufficient to evaporate the falling liquid fraction, to evaporate a portion of the falling liquid fraction in an evaporation amount in kg/hr corresponding to 1 to 15% by weight of the total amount in kg/hr of the liquid fraction introduced into the third reboiler, per one pass of the liquid fraction through the third reboiler; (K) the resultant evaporated and non-evaporated portions of the liquid fraction are withdrawn from the third reboiler and returned into the third distillation column through a returning inlet thereof located above the level of the liquid fraction accumulated in the bottom portion of the third distillation column; and (L) the returned evaporated portion in the third distillation column heat-exchanges to the recovered liquid fraction fed into the third distillation column, to evaporate the heat-deteriorative compound;

(11) the resultant vapor containing the heat-deteriorative compound is recovered through the top outlet of the third column, while allowing the resultant liquid fraction comprising the organic compound having higher boiling temperature than that of the heat-deteriorative compound to be accumulated in the bottom portion of the third distillation column; and

(12) a portion of the liquid fraction accumulated in the bottom portion of the third distillation column is discharged through the bottom outlet of the third distillation column.

DESCRIPTION OF THE PREFERRED EMBODIMENTS

Figure 1:
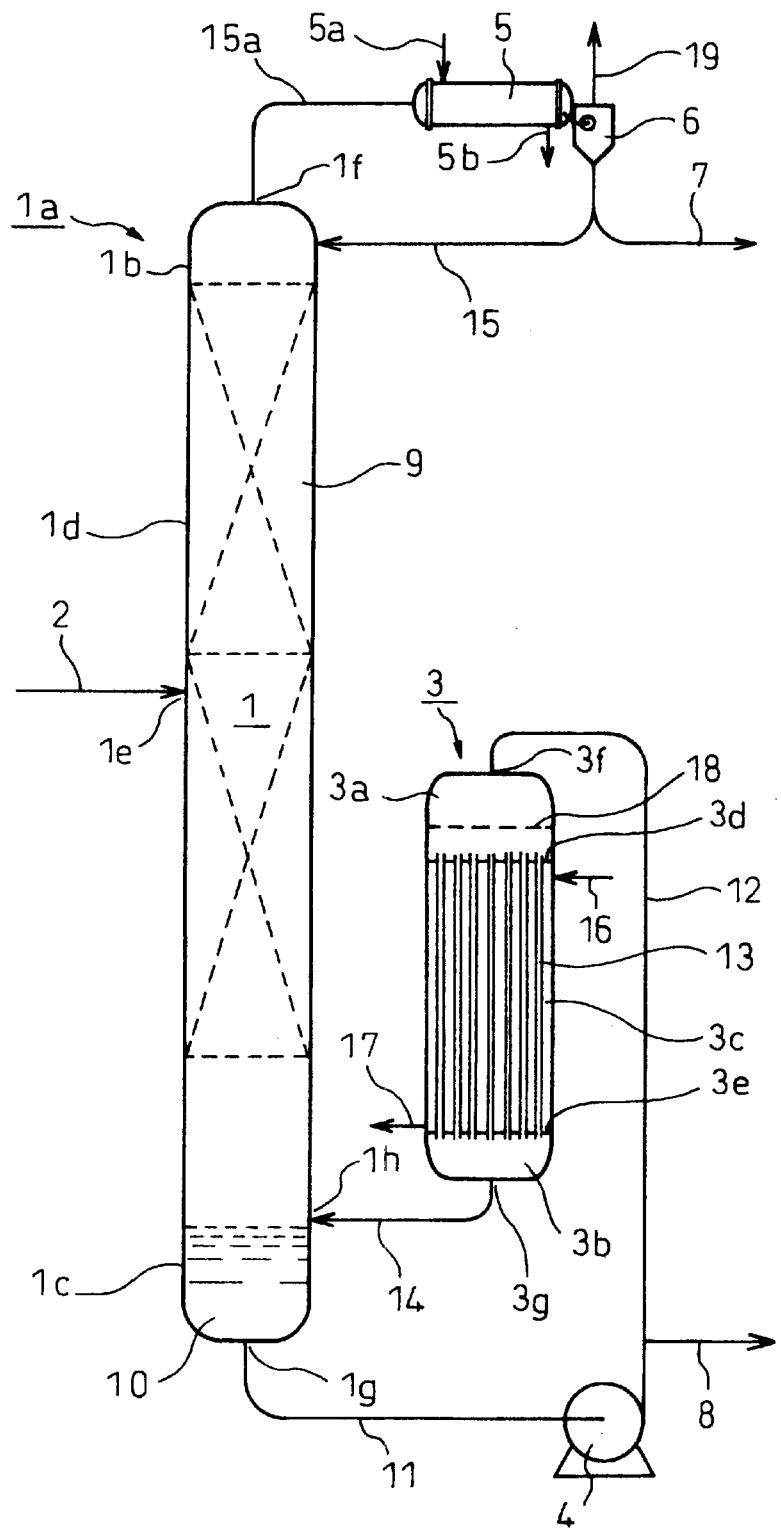
FIG. 1 is an explanatory diagram showing an embodiment of the process of the present invention for refining a heat-deteriorative compound contained in a multi-component liquid by a distillation procedure.

The process of the present invention can be carried out by using, for example, the distillation apparatus as shown in FIG. 1.

In FIG. 1, a distillation apparatus 1a for the process of the present invention comprises a distillation column 1 and a liquid film-falling reboiler 3. The distillation column 1 is provided with a top portion 1b, a bottom portion 1c and a middle portion 1d located between the top and bottom portions 1b and 1c. In the middle portion 1d, a fractionating device 9 is fixed. The fractionating device includes packed column type and multi-tray type fractionating devices. Also, a liquid mixture feed line 2 for feeding a multi-component liquid mixture is connected to the middle portion 1d of the distillation column 1 through a middle inlet 1e.

The liquid film-falling reboiler 3 comprises a top chamber 3a, a bottom chamber 3b and a heating chamber 3c formed between the top chamber 3a and the bottom chamber 3b and partitioned from the top chamber 3a by an upper partition 3d and from the bottom chamber 3b by an lower partition 3e.

The reboiler 3 has a plurality of heat conductive pipes 13 which are spaced from each other and vertically arranged in the heating chamber 3c in such a manner that the upper ends of the vertical pipes 13 open to the top chamber 3a and the lower ends of the vertical pipes 13 open to the bottom chamber 3b. The heating chamber 3c has an inlet located in an upper portion thereof and connected to a heating medium-supply line 16 through which a heating medium, for example, a heating oil or steam, is fed from a heating medium supply source (not shown) into the heating chamber 3c, and an outlet located in a lower portion thereof and connected to a heating medium-discharge line 17 through which the heating medium is discharged from the heating chamber 3c.

The distillation column 1 has a top outlet 1f located in the top portion 1b, and a bottom outlet 1g located in the bottom portion 1c. The bottom portion 1c of the distillation column 1 is connected to the top chamber 3a of the reboiler 3 through the bottom outlet 1g, a delivery line 11, a liquid transporting means 4, a liquid line 12 and a top inlet 3f located in the top chamber 3a. Also, the bottom chamber 3b of the reboiler 3 is connected to the bottom portion 1c of the distillation column 1 through a bottom outlet 3g located in the bottom chamber 3b, a returning line 14 and a bottom inlet 1h of the distillation column 1. The bottom inlet 1h is located above and close to a level of a liquid fraction 10 generated from the multi-component liquid mixture and accumulated in the bottom portion 1c. A recovery line 8 is connected to the liquid line 12 at a location downstream from the liquid transporting means 4. In the top chamber 3a of the reboiler 3, a liquid distributing plate 18 is optionally arranged between the top inlet 3f and the open upper ends of the vertical pipes 13.

The top portion 1b of the distillation column 1 is connected to a cooler 5 through the top outlet 1f and a vapor fraction delivery line 15a. The cooler 5 is connected to a cooling medium-feeding line 5a and a cooling medium-discharging line 5b. Also, the cooler 5 is connected to a vapor-liquid-separating vessel 6. The separator 6 is connected to a vapor-delivery line 19 and a liquid-returning line 15. Also, a liquid-recovery line 7 is connected to the separating vessel 6.

Referring to FIG. 1, the process of the present invention is carried out as follows.

(1) A multi-component liquid mixture comprising a lower boiling temperature component and a higher boiling temperature component containing a heat-deteriorative compound is fed from a supply source thereof (not shown) into the middle portion 1d of the distillation column 1 through a liquid mixture feed line 2 and a middle inlet 1e.

(2) The fed liquid mixture is distilled in the distillation column 1 to generate a vapor fraction comprising the lower boiling temperature component and a liquid fraction comprising the higher boiling temperature component. The vapor fraction is fractionated by the fractionating device 9 arranged in the middle portion 1d while passing upward through the fractionating device 9, and the non-evaporated liquid fraction 10 is accumulated in the bottom portion 1c. The distillation is carried out in the following manner.

(A) The liquid fraction 10 is withdrawn from the bottom portion 1c through the bottom outlet 1g of the distillation column 1 and introduced into the reboiler 3 through the delivery line 11, the liquid-transporting means (liquid pump) 4, a liquid line 12 and a top inlet 3f of the reboiler 3.

(B) The introduced liquid fraction passes through the top chamber 3a and is evenly distributed, optionally through the liquid distributing plate 18, into the open upper ends of the vertical pipes 13; and falls in the form of liquid films along inner surfaces of the vertical pipes 13. Simultaneously, the falling liquid fraction films along the inner surfaces of the vertical pipes 13 are heated by the heating medium which is supplied through the supply line 16, passes through the heating chamber 3c and is discharged through the discharge line 17, at a temperature lower than the heat deterioration-starting temperature of the heat-deteriorative compound but high enough to evaporate the liquid fraction, to such an extent that a portion of the falling liquid fraction is evaporated in an evaporation amount in kg/hr corresponding to 1 to 15% by weight of the total amount in kg/hr of the liquid fraction introduced into the reboiler 3, per pass of the liquid fraction through the reboiler 3.

(C) The evaporated and non-evaporated portions generated from the liquid fraction and passed through the vertical pipes 13 are returned into the bottom portion 1c of the distillation column 1 through the bottom chamber 3b, the bottom outlet 3g, the returning line 14 and the bottom inlet 1h of the distillation column 1. The bottom inlet 1h is located above and close to the level of the liquid fraction accumulated in the bottom portion 1c of the distillation column 1.

(D) In the mixture returned into the bottom portion 1c of the distillation column, the non-evaporated and returned liquid portion is accumulated in the bottom portion 1c of the distillation column 1 and the evaporated and returned vapor portion flows upward through the distillation column 1 and comes into contact with the multi-component liquid mixture fed into the distillation column through the middle inlet 1e, to exchange a heat owned by the vapor portion to the liquid mixture. As a result of the heat-exchange, the low boiling temperature component of the liquid mixture is evaporated to generate the vapor fraction, and a portion of the returned vapor portion is liquefied and mixed into the liquid fraction separated from the vapor fraction. Also, the remaining portion of the returned vapor portion is not liquefied and is mixed into the vapor fraction.

(3) The resultant vapor fraction comprising the lower boiling temperature component is delivered through the top outlet 1f of the distillation column 1, and the resultant liquid fraction comprising the higher boiling temperature component containing the heat-deteriorative compound is accumulated in the bottom portion 1c of the distillation column 1.

(4) A portion of the liquid fraction accumulated in the bottom portion 1c is recovered through the recovery line 8. The recovered liquid fraction comprises the high boiling temperature component and thus contains the target heat-deteriorative compound in an increased concentration.

The vapor fraction generated in the distillation column is refined by passing through the fractionating device 9, is delivered from the top portion 1b through the top outlet if and a delivery line 15a, and then is introduced into the cooler 5. In the cooler 5, the vapor fraction is cooled by a cooling medium which is fed through the line 5a and delivered through the line 5b, to allow a portion of the vapor fraction to be condensed. The resultant vapor-liquid mixture is introduced into the vapor-liquid separating vessel 6 in which the mixture is separated into a vapor portion and a liquid portion. A portion of the liquid portion is returned into the top portion 1b of the distillation column 1 through a return line 15 and the remaining portion of the liquid portion is recovered through a recovery line 7. Also, the vapor portion is delivered from the vapor-liquid separating vessel 6 through a delivery line 19.

In the liquid film-falling reboiler as mentioned above, preferably, a liquid-distributing means 18, for example, a perforated plate having a plurality of holes, or a distributor is arranged in a top chamber 3a of the reboiler 3 into which the liquid fraction 10 is introduced from the bottom portion 1c of the distillation column 1. The liquid distributing means 18 is located above the upper ends of the vertical pipes 13 opening to the top chamber 3a, to evenly distribute the introduced liquid fraction into the upper ends of the vertical pipes 13. The open upper ends of the vertical pipes 13 are supported by the upper partition plate 3d by which the top chamber 3a is separated from the heating chamber 3c, and the lower end portions of the vertical pipes 13 are supported by the lower partition plate 3e by which the bottom chamber 3b is separated from the heating chamber 3c. The upper ends of the vertical pipes 13 are preferably projected upward in a length of 0.5 to 20 mm, more preferably 1 to 10 mm, from the upper partition plate 3d into the upper chamber 3a. Also, one or more notches may be formed in each of the open upper ends of the vertical pipes, to evenly distribute the liquid fraction to the open upper ends of the vertical pipes 13 and to allow the introduced liquid fraction to evenly fall in the form of liquid films along the inner surfaces of the vertical pipes. The lower end portions of the vertical pipes 13 may be projected downward from the lower partition plate 3e into the bottom chamber 3b of the reboiler 3.

The liquid fraction containing the higher boiling temperature component containing the heat-deteriorative compound is withdrawn from the bottom portion 1c of the distillation column 1 through the bottom outlet 1g, the liquid delivery line 11, and the liquid transporting means 4, and a portion of the withdrawn liquid fraction is delivered through the delivery line 8, and optionally introduced into an additional refining procedure to recover the heat deteriorative component and optionally other compounds. Also, the vapor fraction generated in the distillation column 1 is withdrawn from the top portion 1b and optionally introduced into a refining procedure, to recover useful low boiling temperature compounds from the vapor fraction.

In the process of the present invention, the heat-deteriorative compound contained in the multi-component liquid mixture preferably includes heat-sensitive organic compounds having a boiling temperature of 100 to 400° C., more preferably 150 to 350° C. under ambient atmospheric pressure, a melting temperature of −10° C. to 300° C., more preferably 0 to 250° C., and a heat deterioration-starting temperature of 150 to 400° C., more preferably 200 to 300° C.

These heat-deteriorative compounds include aromatic mono- and di-hydroxyl compounds which may be substituted by at least one substituent attached to the aromatic ring and selected from, for example, lower alkyl groups having 1 to 20 carbon atoms and halogen atoms; mono- or more aromatic group (for example, phenyl) esters of aliphatic polycarboxylic acids, for example, diphenyl malonate, diphenyl oxalate and diphenyl carbonate; and alkyl esters of aromatic polycarboxylic acids, for example, alkyl esters of biphenyltetracarboxylic acid and tetraalkyl esters of pyromellitic acid. These compounds may be contained alone or in a mixture of two or more thereof in the multi-component liquid mixture.

The above-mentioned non-substituted aromatic mono- or more- hydroxyl compounds include, for example, phenol and guaiacol which have only one hydroxyl group and catechol, hydroquinone and resorcinol which have two or more hydroxyl groups. The substituted aromatic mono- or more hydroxyl compounds include, for example, 2-methylcatechol, 4-methylcatechol, 2-methylhydroquinone, 2-chlorocatechol and 4-chlorocatechol.

The multi-component liquid mixture to be subjected to the process of the present invention preferably contains the above-mentioned heat-deteriorative compounds in a content of 5% by weight or more, more preferably 10 to 100% by weight, still more preferably 20 to 99.5% by weight.

The multi-component liquid mixture to be subjected to the process of the present invention contains, in addition to the heat-deteriorative compound, at least one heat-stable high boiling temperature compound having a boiling temperature of 200 to 400° C. under ambient atmospheric pressure, and at least one heat-stable low boiling temperature compound having a boiling temperature of 50 to 200° C., more preferably 60 to 150° C. under ambient atmospheric pressure. The multi-component liquid mixture may further contain another organic compounds which are compatible with the above-mentioned organic compounds, to form a liquid mixture (solution).

In the process of the present invention, the heat-stable higher and lower boiling temperature components are preferably capable of dissolving the heat-deteriorative compound to form a solution, or of forming a melt solution containing the heat-deteriorative compound, and each preferably contains one or more heat-stable organic compounds selected from aliphatic alcohols, cycloaliphatic alcohols, ethers, ketones, glycols, aromatic carboxylic acid ethers, aliphatic hydrocarbons, cycloaliphatic hydrocarbons, and aromatic hydrocarbons.

The heat-stable organic compounds usable for the process of the present invention are preferably selected from organic compounds having a higher heat-stability than that of the heat deteriorative compound at a temperature of 100 to 300° C., particularly a heat-deterioration-starting temperature of 10 to 100° C. above that of the heat-deteriorative compound, for example, include aliphatic monohydric alcohols having 1 to 20 carbon atoms, for example, methyl alcohol, ethyl alcohol, n-propyl alcohol, isopropyl alcohol, butyl alcohol, aryl alcohol, hexyl alcohol, and octyl alcohol; L aliphatic dihydric alcohols, for example, ethylene glycol; cycloaiphatic alcohols, for example, cyclohexyl alcohol; ethers, for example, dimethylether, diethylether, methylethylether, methyl-isopropylether, methyl-isobutyl ether and diphenylether; ketones, for example, dimethylketone, diethylketone, diphenylketone; and aliphatic carboxylic acid esters, for example, oxalic acid esters, acetic acid esters, propionic acid esters and dialkyl oxalates.

In the process of the present invention, the multi-component liquid mixture preferably comprises an aromatic hydroxyl compound, for example, hydroquinone or catechol, having a boiling temperature of 150 to 350° C., more preferably 180 to 300° C., under ambient atmospheric pressure, and exhibiting a certain heat-deteriorative property at a temperature of 150 to 300° C., in a content of 50% by weight or more, and other organic compounds resistant to heat-deterioration and compatible with the heat-deteriorative aromatic hydroxyl compound. Preferably, the multi-component liquid mixture is in the form of a liquid mixture (solution) at a temperature of 100 to 300° C.

In the process of the present invention, the liquid fraction withdrawn from the distillation column and introduced into the reboiler fall in the form of a plurality of liquid films along the inner surfaces of the vertical pipes. The falling liquid fraction through the vertical pipes is heated at a temperature lower than the heat deterioration-starting temperature and high sufficient to evaporate the liquid fraction. The evaporation procedure is controlled to such an extent that a portion of the falling liquid fraction is evaporated in an evaporation amount (rate) in kg/hr corresponding to 1 to 15%, preferably 1 to 10%, more preferably 1 to 7%, by weight of the total falling amount (rate) in kg/hr of the liquid fraction introduced into the reboiler, per one pass of the liquid fraction through the reboiler. The controlled evaporation procedure in the reboiler is very important to prevent the heat-deterioration of the heat-deteriorative compound in the reboiler and to minimize breakage of the liquid films of the falling liquid fraction formed on the inner surfaces of the vertical pipes.

In the process of the present invention, the evaporation procedure in the reboiler is carried out under the above-mentioned conditions and preferably the liquid films of the liquid fraction falling through the vertical pipes of the reboiler exhibits a Reynolds' number (Re) of 700 to 10,000, more preferably 750 to 9,000, still more preferably 800 to 8,000.

The heat-deterioration-starting temperature of the heat-deteriorative compound is a temperature at which, or higher than, the deterioration of the compound proceeds, or a temperature at which the compound is deteriorated in a rate of 2% by weight per hour of heating time. The falling liquid films of the liquid fraction are heated in the vertical pipes by a heating medium passing through the heating chamber, and converted to a mixture of "vapor portion and a non-evaporated liquid portion and the vapor-liquid mixture is introduced into the bottom chamber of the reboiler through the open lower ends of the vertical pipes. The evaporation temperature of the falling liquid films of the liquid fraction is represented by an average temperature of the non-evaporated liquid portion measured at the open lower ends of the vertical pipes.

Theoretically speaking, the heat deterioration of the heat-deteriorative compound in the falling liquid films of the liquid fraction in the reboiler is directly governed by the temperature of the back surfaces of the falling, tube-formed liquid films brought in contact with the other heating surfaces of the vertical pipes, the temperature of the evaporation (front) surfaces of the falling, tube-formed liquid films, or a differential temperature between the back surface temperature of the falling, tube-formed liquid films and the outer heating surface temperature of the vertical pipes. In the process of the present invention, the average temperature of the non-evaporated liquid portion in the form of falling liquid films, measured at the open lower ends of the vertical pipes is controlled to the level as mentioned above and represents the evaporation temperature of the falling liquid films through the vertical pipes of the reboiler.

In the process of the present invention, preferably, the evaporation temperature of the falling liquid films of the liquid fraction in the reboiler is preferably controlled to a level of 3° C. or more, more preferably 5 to 50° C., still more preferably 10 to 30° C., below the heat-deterioration-starting temperature of the heat-deteriorative compound. The evaporation temperature of the falling liquid films of the liquid fraction can be established in consideration of the type and dimensions of the liquid film-falling reboiler and in response to the inner pressure of the reboiler, the flow rate of the liquid fraction through the reboiler, and other operative conditions of the reboiler.

When the evaporation amount of the falling liquid films in the reboiler per pass of the liquid fraction through the reboiler is more than 15% by weight based on the total amount of the liquid fraction introduced into the reboiler, the amount of the non-evaporated liquid portion becomes too small, and thus the falling films of the non-evaporated liquid portion are easily broken, the temperature of the falling liquid films is locally increased, and the heat deterioration of the heat-deteriorative compound is certainly increased. Also, when the evaporation amount is lower than the above-mentioned lower limit thereof, the efficiency of the distillation apparatus, namely the reboiler and the distillation column, with respect to the evaporation amount is too low for practical use, and thus the productivity is degraded and an economical disadvantage occurs.

In the establishment of the dimensions of the above-mentioned distillation, a Reynolds' number (Re) of the liquid films of the liquid fraction falling along the inner surfaces of the vertical heat-conductive pipes is preferably considered in addition to the evaporation amount per one pass of the liquid fraction through the reboiler.

The Reynolds' number of the liquid films can be calculated in accordance with equation (3) which is induced from equations (1) and (2):

$$Re = \frac{4}{\mu} \cdot m \quad (1)$$

$$m = \frac{w}{N \cdot \pi \cdot D} \quad (2)$$

$$Re = \frac{4}{\mu} \cdot \frac{w}{N \cdot \pi \cdot D} \quad (3)$$

In equations (1), (2) and (3),

Re represents a Reynolds' number of the falling liquid film through a plurality of vertical heat-conductive pipes, m represents a flow rate of a liquid flowing through the pipes per unit horizontal width of the heat-conductive surface, in kg/m·hr, $\mu$ represents a viscosity of the liquid in kg/m·hr, w represents a flow rate of the liquid in kg/hr, N represents the number of the vertical heat conductive pipes, and D represents an inner diameter of each vertical heat conductive pipe.

Namely, the Reynolds' number can be calculated from the flow rate (w: kg/hr) of the liquid, the viscosity ($\mu$: kg/m·hr), the number of the heat conductive pipes (N), and the inner diameter (D:m) of the heat conductive pipes.

In the process of the present invention, preferably the Reynolds' number (Re) of the falling liquid films of the liquid fraction passing through the reboiler is controlled to 700 to 10,000, more preferably 2,000 to 8,000, still more preferably 3,200 to 7,000.

When the Reynolds' number of the liquid films falling along the inner surface of the vertical heat conductive pipes of the reboiler is too low, the conduction of heat from the heating medium to the liquid films through the heat-conductive pipes is unsatisfactory, the heat-conductive area necessary to evaporate the liquid film of a desired extent becomes too large, the cost of the evaporation device increases, the temperature of the boundaries between the falling liquid films and the heat-conductive surfaces of the vertical pipes becomes too high and thus the deterioration of the heat deteriorative compound in the falling liquid films undesirably increases.

In the process of the present invention, the liquid films of the liquid fraction falling along the inner surfaces of the vertical heat-conductive pipes of the reboiler preferably have an average liquid film thickness large enough to prevent the breakage of the liquid films. Generally the average thickness of the falling liquid films is preferably 0.1 to 5 mm, more preferably 0.5 to 2 mm.

Also, when the Reynolds' number of the falling liquid films is 3,200 or more the average thickness of the falling liquid films can be calculated in accordance with equation (4).

$$\delta = 0.302 \cdot \left[\frac{3 \cdot \mu^2}{g \cdot \rho^2}\right]^{1/3} \cdot \left[\frac{Re}{4}\right]^{8/15} \quad (4)$$

In equation (4),

δ represents an average thickness in m of liquid films, $\mu$ represents a viscosity in kg/m·hr of the falling liquid films, g represents an acceleration of gravity of $1.27 \times 10^8$ m/hr$^2$, ρ represents a density in kg/m$^3$ of the falling liquid films, and Re represents a Reynolds' number of the falling liquid films.

The refining process of the present invention for the heat-deteriorative compound by distillation is preferably utilized to refine the heat-deteriorative compound contained in a multi-component liquid mixture and to separate other components from each other.

In the process of the present invention, when the higher boiling temperature component contained in the liquid fraction recovered in the recovery step (4) contains, in addition to the heat-deteriorative compound, at least one organic compound having a boiling temperature lower than that of the heat-deteriorative compound, the recovered liquid fraction from the recovery step (4) is subjected to the further refining procedures comprising the steps of:

(5) feeding the recovered liquid fraction into an additional distillation column having a top outlet located in a top portion of the additional distillation column and a bottom outlet located in a bottom portion of the additional distillation column, the bottom outlet being connected to an additional liquid film-falling reboiler having a plurality of heat-conductive vertical pipes spaced from each other and arranged in a heating chamber through which a heating medium passes;

(6) distilling the fed liquid fraction in the additional distillation column to generate a liquid fraction comprising the heat-deteriorative compound and a vapor fraction comprising the organic compound having a lower boiling temperature than that of the heat-deteriorative compound, in such a manner that (E) the liquid fraction is withdrawn through the bottom outlet of the additional distillation column and introduced into the additional reboiler to allow the introduced liquid fraction to fall in the form of films along inner surfaces of the vertical pipes of the additional reboiler; (F) the falling liquid fraction passing through the vertical pipes is heated by the heating medium passing through the heating chamber at a temperature lower than the heat deterioration-starting temperature of the heat-deteriorative compound but sufficient to evaporate the falling liquid fraction, to evaporate a portion of the falling liquid fraction in an evaporation amount in kg/hr corresponding to 1 to 15% by weight of the total amount in kg/hr of the liquid fraction introduced into the additional reboiler, per one pass of the liquid fraction through the additional reboiler; (G) the resultant evaporated and non-evaporated portions of the liquid fraction are withdrawn from the additional reboiler and returned into the additional distillation column through a returning inlet thereof located above the level of the liquid fraction accumulated in the bottom portion of the additional distillation column; and (H) the returned evaporated portion in the additional distillation column heat-exchanges to the recovered liquid fraction fed into the additional distillation column, to evaporate the organic compound having the lower boiling temperature than that of the heat-deteriorative compound;

(7) delivering the resultant vapor comprising the organic compound having the lower boiling temperature than that of the heat-deteriorative compound through the top outlet of the additional distillation column, while allowing the resultant liquid fraction comprising the heat-deteriorative compound to accumulate in the bottom portion of the additional distillation column; and (8) recovering a portion of the liquid fraction accumulated in the bottom portion of the additional distillation column and comprising the heat-deteriorative compound through the bottom outlet of the additional distillation column.

In the distilling step (6), the film of the liquid fraction falling along the inner surfaces of the vertical pipes of the additional reboiler preferably exhibits a Reynolds' number (Re) of 700 to 10,000, more preferably 2,000 to 8,000, still more preferably 3,200 to 7,000.

In the above-mentioned process of the present invention, when the liquid fraction recovered from the additional distillation column in recovery step (8) contains, in addition to the heat-deteriorative compound, at least one organic compound having a higher boiling temperature than that of the heat-deteriorative compound and the recovered liquid fraction from the recovery step (8) is further subjected to the further additional refining procedures comprising the steps of:

(9) feeding the recovered liquid fraction from the additional distillation column into a further additional distillation column having a top outlet located in a top portion of the further additional distillation column and a bottom outlet located in a bottom portion of the further additional distillation column, the bottom outlet being connected to a further additional liquid film-falling reboiler having a plurality of heat conductive vertical pipes spaced from each other and arranged in a heating chamber through which a heating medium passes;

(10) distilling the fed liquid fraction in the further additional distillation column to generate a vapor fraction comprising the heat-deteriorative compound and a liquid fraction comprising the organic compound having the higher boiling temperature than that of the heat-deteriorative compound, in such a manner that (I) the liquid fraction in the further additional distillation column is withdrawn through the bottom outlet of the further additional distillation column and introduced into the further additional reboiler to allow the introduced liquid fraction to fall in the form of films along inner surfaces of the vertical pipes of the further additional reboiler; (J) the falling liquid fraction through the vertical pipes is heated by the heating medium passing through the heating chamber at a temperature lower than the heat-deterioration-starting temperature of the heat-deteriorative compound but sufficient to evaporate the falling liquid fraction, to evaporate a portion of the falling liquid fraction in an evaporation amount in kg/hr corresponding to 1 to 15% by weight of the total amount in kg/hr of the liquid fraction introduced into the further additional reboiler, per one pass of the liquid fraction through the further additional reboiler; (K) the resultant evaporated and non-evaporated portions of the liquid fraction is withdrawn from the further additional reboiler and is returned into the further additional distillation column through a returning inlet thereof located above the level of the liquid fraction accumulated in the bottom portion of the further additional distillation column; and (L) the returned evaporated portion in the further additional distillation column heat-exchanges to the recovered liquid fraction into the further additional distillation column, to evaporate the heat-deteriorative compound;

(11) recovering the resultant vapor containing the heat-deteriorative compound through the top outlet of the further additional distillation column, while allowing the resultant liquid fraction comprising the organic compound having a higher boiling temperature than that of the heat-deteriorative compound to accumulate in the bottom portion of the further additional distillation column; and

(12) discharging a portion of the liquid fraction accumulated in the bottom portion through the bottom outlet of the further additional distillation column.

In the distilling step (10), the liquid film of the liquid fraction falling along the inner surfaces of the vertical pipes of the further additional preferably exhibits a Reynolds' number (Re) of 700 to 10,000, more preferably 2,000 to 8,000, still more preferably 3,200 to 7,000.

Figure 2:
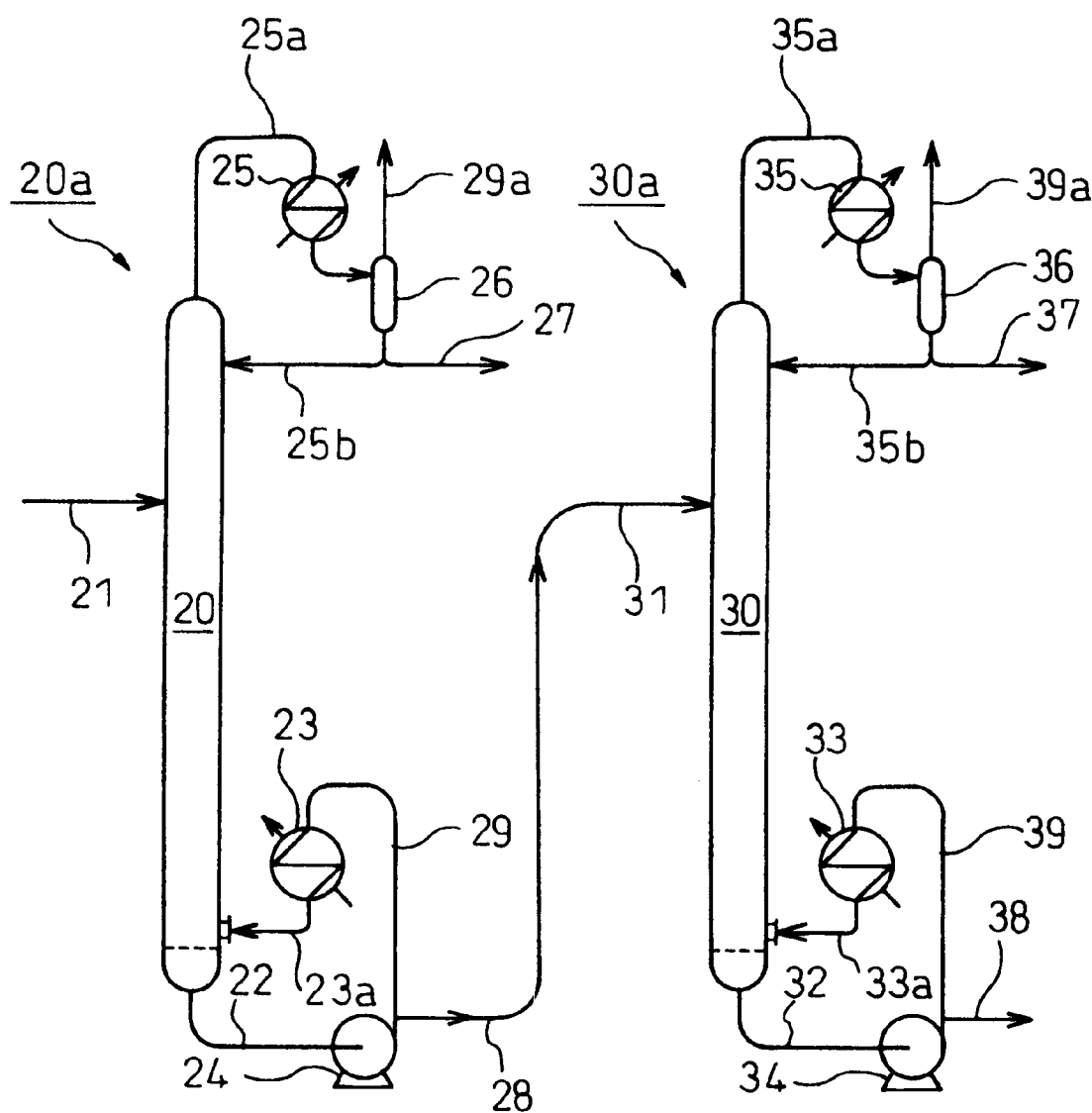
FIG. 2 is an explanatory diagram showing another embodiment of the process of the present invention in which the heat-deteriorative compound contained in a liquid fraction delivered from the distillation procedure as shown in FIG. 1 is further refined by an additional distillation procedure.

When the multi-component liquid mixture comprises a lower boiling temperature component and a higher boiling temperature component which comprises a heat-deteriorative compound and at least one organic compound having a boiling temperature higher than that of the lower boiling temperature component and lower than that of the heat-deteriorative compound, the liquid mixture is subjected to the refining process of the present invention using a distillation apparatus 20a and an additional distillation apparatus 30a connected to each other. Referring to FIG. 2, a multi-component liquid mixture is fed into a middle portion of a distillation column 20 of the distillation apparatus 20a through a liquid mixture-feed line 21. In the distillation column 20, the liquid mixture is separated to a vapor fraction and a liquid fraction. The liquid fraction is accumulated in a bottom portion of the distillation column and circulated, through a withdrawing line 22, a liquid transporting means (liquid pump) 24, a liquid line 29, a reboiler 23 and a returning line 23a, into the bottom portion of the distillation column 20 at a is location close to and above the level surface of the liquid fraction accumulated in the bottom portion. In the reboiler 23 which has the same constitution as shown in FIG. 1, the liquid fraction is distributed to a plurality of vertical heat-conductive pipes and falls in the form of liquid films along the inner surfaces of the vertical pipes. The falling liquid films of the liquid fraction are heated in the same manner as shown in FIG. 1 and a portion of the falling liquid fraction is evaporated in an evaporation amount in kg/hr corresponding to 1 to 15% by weight of the total amount in kg/hr of the liquid fraction introduced into the reboiler 23, per one pass of the liquid fraction through the reboiler 23. The resultant heated mixture of the evaporated vapor portion and the non-evaporated liquid portion of the liquid fraction is withdrawn from the reboiler 23 and introduced into the bottom portion of the distillation column 20 through the returning line 23a. The returned evaporated vapor portion generated from the liquid fraction heat-exchanges to the multi-component liquid mixture fed into the distillation column 20 to generate a vapor fraction comprising the lower boiling temperature component.

The vapor fraction is delivered from the top portion of the distillation column 20 through a delivery line 25a and introduced into a cooler 25. The resultant cooled vapor/liquid mixture is introduced into a vapor/liquid separator 26. The separated vapor is delivered from the separator 26 through a delivery line 29a and a portion of the separated liquid is returned into the top portion of the distillation column 20 through a returning line 25b. Also, the remaining portion of the separated liquid is recovered from the separator 26 through a recovery line 27.

Further, a portion of the liquid fraction withdrawn from the bottom portion of the distillation column 20 is recovered through a recovery line 28 connected to a liquid line 29 at a location downstream from the liquid-transporting means (liquid pump) 24.

The recovered liquid fraction from the distillation apparatus 20a through the recovery line 28 is supplied to an additional distillation apparatus 30a. Namely, the recovered liquid fraction is fed into a middle portion of an additional distillation column 30 through a feed line 31. The fed liquid is a liquid mixture comprising the higher boiling temperature component which comprises the heat-deteriorative compound and at least one organic compound having a boiling temperature lower than that of the heat-deteriorative compound.

In the additional distillation apparatus 30a shown in FIG. 2, the fed liquid mixture is distilled as follows.

In the additional distillation column 30, the fed liquid mixture is separated into a vapor fraction comprising the organic compound having a boiling temperature lower than that of the heat-deteriorative compound and a liquid fraction comprising the heat-deteriorative compound.

The liquid fraction is accumulated in a bottom portion of the additional distillation column 30 and circulated, through a withdrawing line 32, a liquid-transporting means (liquid pump) 34, a liquid line 39, an additional reboiler 33 and a returning line 33a, into the bottom portion of the additional distillation column 30 at a location close to and above the level surface of the liquid fraction accumulated in the bottom portion of the additional distillation column 30. In the additional reboiler 33 which has the same constitution as shown in FIG. 1, the liquid fraction withdrawn from the additional distillation column 30 is distributed to a plurality of vertical heat-conductive pipes and falls in the form of liquid films along the inner surfaces of the vertical pipes. The falling liquid films of the liquid fraction are heated in the same manner as shown in FIG. 1 and a portion of the falling liquid fraction is evaporated in an evaporation amount in kg/hr corresponding to 1 to 15% by weight of the total amount in kg/hr of the liquid fraction introduced into the additional reboiler 33, per one pass of the liquid fraction through the additional reboiler 33. The resultant heated mixture of the evaporated vapor portion and the non-evaporated liquid portion of the liquid fraction is withdrawn from the additional reboiler 33 and introduced into the bottom portion of the additional distillation column 30 through the returning line 33a. The returned evaporated vapor portion generated from the liquid fraction heat-exchanges to the liquid mixture fed into the additional distillation column 30 to generate a vapor fraction comprising the organic compound having a lower boiling temperature than that of the heat-deteriorative compound.

The vapor fraction is delivered from the top portion of the additional distillation column 30 through a delivery line 35a and introduced into a cooler 35. The resultant cooled vapor/liquid mixture is introduced into a vapor/liquid separator 36. The separated vapor is delivered from the separator 36 through a recovery line 39a, the separated liquid is recovered from the separator 36 through recovery line 37. Optionally a portion of the separated liquid is returned into the top portion of the additional distillation column 30 through a returning line 35b.

Further, a portion of the liquid fraction withdrawn from the bottom portion of the additional distillation column 30 is recovered through a recovery line 38 connected to a liquid line 39 at a location downstream from the liquid-transporting means (liquid pump) 34.

The vapor portion delivered through the delivery line 39a is discharged to the ambient atmosphere, or burnt in the ambient atmosphere, or is transported to a vacuum pump. The liquid portion recovered through the recovery line 37 may be fed into a fractionation procedure to fractionate the liquid portion and to recover the resultant individual compounds.

When the delivered liquid portion from the recovery line 37 contains the heat-deteriorative compound, the delivered liquid portion may be fed into a further additional refining procedure.

Also, when the liquid fraction recovered from the bottom portion of the additional distillation column 30 through the recovery line 38 in step (8), contains, in addition to the heat-deteriorative compound, at least one organic compound having a higher boiling temperature than that of the heat-deteriorative compound, the recovered liquid fraction from step (8) is further refined by the following steps (9) to (12).

(9) The recovered liquid fraction from the additional distillation column is fed into a further additional distillation column having a top outlet located in a top portion of the further additional distillation column and a bottom outlet located in a bottom portion of the further additional distillation column, the bottom outlet being connected to a further additional liquid film-falling reboiler having a plurality of heat conductive vertical pipes spaced from each other and arranged in a heating chamber through which a heating medium passes.

(10) The fed liquid fraction in the further additional distillation column is distilled to generate a vapor fraction comprising the heat-deteriorative compound and a liquid fraction comprising the organic compound having the higher boiling temperature than that of the heat-deteriorative compound, in such a manner that (I) the liquid fraction in the further additional distillation column is withdrawn through the bottom outlet of the further additional distillation column and introduced into the further additional reboiler to allow the introduced liquid fraction to fall in the form of films along inner surfaces of the vertical pipes of the further additional reboiler; (J) the falling liquid fraction passing through the vertical pipes is heated by the heating medium passing through the heating chamber at a temperature lower than the heat-deterioration-starting temperature of the heat-deteriorative compound but sufficient to evaporate the falling liquid fraction, to evaporate a portion of the falling liquid fraction in an evaporation amount in kg/hr corresponding to 1 to 15% by weight of the total amount in kg/hr of the liquid fraction introduced into the further additional reboiler, per one pass of the liquid fraction through the further additional reboiler; (K) the resultant evaporated and non-evaporated portions of the liquid fraction are withdrawn from the further additional reboiler and are returned into the further additional distillation column through a returning inlet thereof located above the level of the liquid fraction accumulated in the bottom portion of the further additional distillation column; and (L) the returned evaporated portion in the further additional distillation column heat-exchanges with the recovered liquid fraction into the further additional distillation column, to evaporate the heat-deteriorative compound. (11) The resultant vapor containing the heat-deteriorative compound is recovered through the top outlet of the further additional distillation column, while allowing the resultant liquid fraction comprising the organic compound having higher boiling temperature than that of the heat-deteriorative compound to accumulate in the bottom portion of the further additional distillation column.

(12) A portion of the liquid fraction accumulated in the bottom portion is discharged through the bottom outlet of the further additional distillation column.

Figure 3:
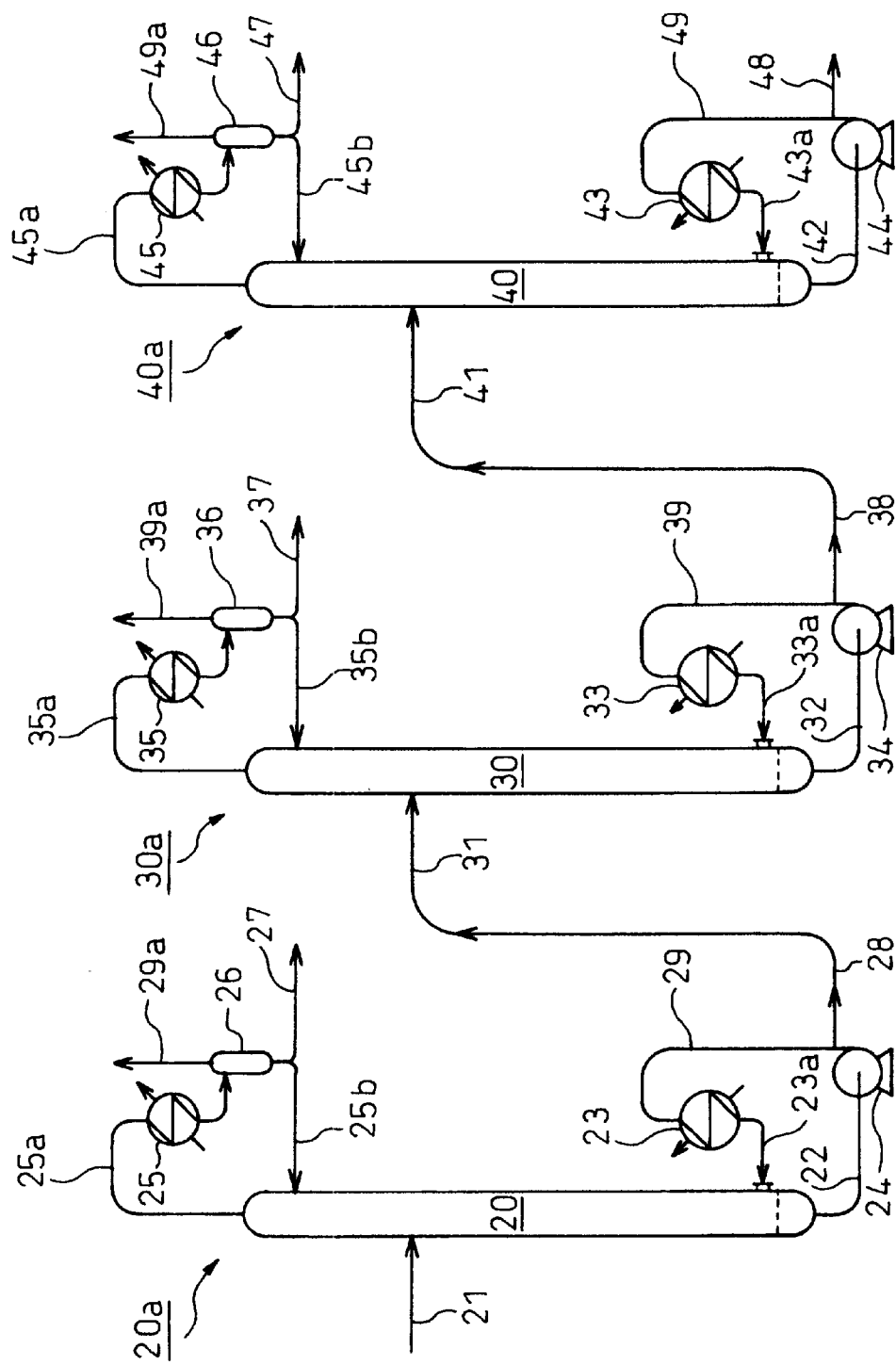
FIG. 3 is an explanatory diagram showing still another embodiment of the process of the present invention in which the heat-deteriorative compound contained in a liquid fraction obtained through the distillation procedure and the additional distillation procedure as shown in FIG. 2 is further refined by a further additional distillation procedure.

Referring to FIG. 3, when the multi-component liquid mixture comprises a lower boiling temperature component and a higher boiling temperature component which comprises a heat-deteriorative compound, at least one organic compound (A) having a boiling temperature lower than that of the heat-deteriorative compound and at least one organic compound (B) having a boiling temperature higher than that of the heat deteriorative component, the multi-component liquid mixture is fed into the distillation apparatus 20a and is distilled therein by the above-mentioned procedures. The resultant vapor portion comprising the lower boiling temperature component is delivered from the top portion of the distillation column 20.

The resultant liquid fraction is circulated through the reboiler 23 by the above-mentioned procedures, and a portion of the liquid fraction is recovered from the bottom portion of the distillation column 20.

The recovered liquid fraction is fed into the additional distillation apparatus 30a and separated into a vapor fraction comprising the lower boiling temperature compound (A) and a liquid fraction comprising the heat-deteriorative compound and the higher boiling temperature compound (B) by the above-mentioned procedures. A portion of the vapor fraction is recovered from the top portion of the additional distillation column 30 and the remaining portion is returned into the top portion of the additional distillation column. The liquid fraction is circulated through the additional refiner 33 by the same procedures as mentioned above.

A portion of the liquid fraction generated in the additional distillation column 30 is recovered from the bottom portion of the additional distillation column 30 through the recovery line 38.

The recovered liquid fraction is a liquid mixture comprising the heat-deteriorative compound and the higher boiling temperature compound (B).

The liquid mixture is fed into a middle portion of a further additional distillation apparatus 40a through a feed line 41.

In the further additional distillation apparatus 40a in FIG. 3, the fed liquid mixture is further distilled as follows.

In the further additional distillation column 40, the fed liquid mixture is separated into a vapor fraction comprising the heat-deteriorative compound and a liquid fraction comprising the higher boiling temperature compound (B).

The liquid fraction is accumulated in a bottom portion of the further additional distillation column 40 and circulated, through a withdrawing line 42, a liquid-transporting means (liquid pump) 44, a liquid line 49, a further additional reboiler 43 and a returning line 43a, into the bottom portion of the further additional distillation column 40 at a location close to and above the level surface of the liquid fraction accumulated in the bottom portion of the further additional distillation column 40. In the further additional reboiler 43 which has the same constitution as shown in FIG. 1, the liquid fraction withdrawn from the further additional distillation column 40 is distributed to a plurality of vertical heat-conductive pipes and falls in the form of liquid films along the inner surfaces of the vertical pipes. The falling liquid films of the liquid fraction are heated in the same manner as shown in FIG. 1 and a portion of the falling liquid fraction is evaporated in an evaporation amount in kg/hr corresponding to 1 to 15% by weight of the total amount in kg/hr of the liquid fraction introduced into the reboiler 43, per one pass of the liquid fraction through the further additional reboiler 43. The resultant heated mixture of the evaporated vapor portion and the non-evaporated liquid portion of the liquid fraction is withdrawn from the further additional reboiler 43 and introduced into the bottom portion of the further additional distillation column 40 through the returning line 43a. The returned evaporated vapor portion generated from the liquid fraction heat-exchanges with the liquid mixture fed into the further additional distillation column 40 to generate a vapor fraction comprising the heat-deteriorative compound.

The vapor fraction is delivered from the top portion of the further additional distillation column 40 through a delivery line 45a and introduced into a cooler 45. The resultant cooled vapor/liquid mixture is introduced into a vapor/liquid separator 46. The separated vapor is delivered from the separator 46 through a delivery line 49a. The separated liquid comprising the heat-deteriorative compound is recovered from the separator 46 through a recovery line 47. Optionally, a portion of the separated liquid is returned into the top portion of the further additional distillation column 40 through a returning line 45b.

Further, a portion of the liquid fraction withdrawn from the bottom portion of the further additional distillation column 40 is recovered through a recovery line 48 connected to a liquid line 49 at a location downstream from the liquid-transporting means (liquid pump) 44.

The vapor portion delivered through the delivery line 49a is discharged to the ambient atmosphere, or burnt in the ambient atmosphere, or is transported to a vacuum pump. The liquid portion recovered through the recovery line 47 and comprising the heat-deteriorative compound may be fed into a refining procedure.

The liquid portion delivered through the recovery line 48 is optionally fed into a fractionation procedure to recover the individual components. When the delivered liquid fraction from the recovery line 48 contains the heat-deteriorative compound, the delivered liquid fraction may be fed into a further additional recovery procedure for the heat-deteriorative compound.

In the further additional reboiler 43, the falling liquid films formed on the inner surfaces of the vertical heat conductive pipes preferably exhibit a Reynolds' number (Re) of 700 to 10,000, more preferably 2,000 to 8,000, still more preferably 3,200 to 7,000.

The process of the present invention can be utilized to separate a multi-component liquid mixture comprising a heat-deteriorative compound and other organic compounds into individual compounds by distillation-refining procedures. Particularly, the process of the present invention is useful for distilling a multi-component liquid mixture obtained, as a reaction product-containing liquid, by reacting an aromatic polyhydroxyl compound, for example, catechol, with a lower alkyl alcohol, for example, methyl alcohol, and comprising non-reacted lower alkyl alcohol, for example, methyl alcohol, non-reacted aromatic polyhydroxyl compound, for example, catechol, monoalkyl ether of the aromatic polyhydroxyl compounds, for example, guaiacol, and by-product compounds, to recover the above-mentioned individual compounds separated from each other. For this distillation, the apparatus shown in FIG. 2 and comprising a distillation apparatus 20a and an additional distillation apparatus 30a are connected to each other.

In an embodiment of the present invention, the multi-component liquid mixture may be supplied from a reaction of a lower alkyl alcohol having 1 to 4 carbon atoms with an aromatic compound having two or more hydroxyl groups, to produce an alkyl ether of the aromatic di- or more hydroxyl compound. The resultant multi-component liquid mixture comprises a lower boiling temperature component comprising the non-reacted lower alkyl alcohol, and a higher boiling temperature component comprising the non-reacted aromatic di- or more hydroxyl compound which is heat-deteriorative and at least one alkyl ether of the aromatic di- or more hydroxyl compound which ether has a lower boiling temperature than the aromatic di- or more hydroxyl compound. From the multi-component liquid mixture, the heat-deteriorative aromatic di- or more hydroxyl compound is refined by the procedures as shown in FIGS. 1 and 2.

(1) The multi-component liquid mixture is fed into a middle portion of a first distillation column 20 having a top outlet located in a top portion of the first distillation column 20 and a bottom outlet located a bottom portion of the first distillation column 20, the bottom outlet being connected to a first liquid film-falling reboiler 23 having a plurality of heat-conductive vertical pipes spaced from each other and arranged in a heating chamber through which a heating medium passes, as shown in FIG. 2, through a feed line 21.

(2) The fed multi-component liquid mixture is distilled in the first distillation column 20 to generate a vapor fraction comprising the lower boiling temperature component and a liquid fraction comprising the higher boiling temperature component, in such a manner that (A) the liquid fraction is withdrawn through the bottom outlet of the first distillation column 20, a delivery line 22, a liquid transporting means 24 and a liquid line 29, and introduced into the first reboiler 23 in which the introduced liquid fraction falls in the form of films along the inner surfaces of the vertical pipes as shown in FIG. 1; (B) the falling liquid fraction is heated by the heating medium passing through the heating chamber at a temperature lower than the heat-deterioration-starting temperature of the aromatic compound having two or more hydroxyl groups but sufficient to evaporate the failing liquid fraction, to evaporate a portion of the falling liquid fraction in an evaporation amount in kg/hr corresponding to 1 to 15% by weight of the total amount in kg/hr of the liquid fraction introduced into the first reboiler 23, per one pass of the liquid fraction through the first reboiler 23; (C) the resultant evaporated and non-evaporated portions of the liquid fraction are withdrawn from the first reboiler 23 and returned into the first distillation column 20 through a returning line 23a and a returning inlet of the first distillation column located above the level of the liquid fraction accumulated in the bottom portion of the first distillation column 20; and (D)

the evaporated portion of the returned liquid fraction heat-exchanges with the multi-component liquid mixture fed into the first distillation column 20 to evaporate the lower boiling temperature component, containing the lower alkyl alcohol.

(3) The resultant vapor fraction comprising the lower boiling temperature component is delivered by a delivery line 25a through the top outlet of the first distillation column 20, while allowing the resultant liquid fraction comprising the higher boiling temperature component to be accumulated in the bottom portion of the first distillation column 20. The delivered vapor fraction through the delivery line 25a is cooled by a cooler 25 to convert the vapor fraction to a vapor/liquid mixture. The vapor/liquid mixture is introduced into a vapor/liquid separator 26 to separate a liquid portion comprising mainly the lower alkyl alcohol and a vapor portion. The liquid portion is recovered through a recovery line 27. Optionally, a portion of the liquid portion is returned into the top portion of the first distillation column 20, through a returning line 25b. The vapor portion is discharged through a discharge line 29.

(4) A potion of the liquid fraction accumulated in the bottom portion of the first distillation column 20 and comprising the higher boiling temperature component containing the heat-deteriorative aromatic di- or more hydroxyl component is recovered through the bottom outlet of the first distillation column 20 and a delivery line 28.

(5) The recovered liquid fraction, which comprises the higher boiling temperature component comprising the heat-deteriorative aromatic di- or more hydroxyl compound and the alkyl ether of the heat-deteriorative aromatic compound having a boiling temperature lower than that of the heat-deteriorative compound, is fed into a middle portion of a second distillation column 30 having a top outlet located in a top portion of the second distillation column 30 and a bottom outlet located in a bottom portion of the second distillation column 30, the bottom outlet being connected to a second liquid film-falling reboiler 33 having a plurality of heat-conductive vertical pipes spaced from each other and arranged in a heating chamber through which a heating medium passes through a feed line 31.

(6) The fed liquid fraction is distilled in the second distillation column 30 to generate a liquid fraction comprising the heat-deteriorative aromatic compound and a vapor fraction comprising the alkyl ether of the heat-deteriorative aromatic compound having a lower boiling temperature than that of the heat-deteriorative aromatic compound, in such a manner that (E) the liquid fraction in the second distillation column is withdrawn through the bottom outlet of the second distillation column 30, a delivery line 32, a liquid transporting means 34 and a liquid line 39, and introduced into the second reboiler 33 to allow the introduced liquid fraction to fall in the form of liquid films along inner surfaces of the vertical pipes of the second reboiler; (F) the falling liquid fraction through the vertical pipes is heated by the heating medium passing through the heating chamber at a temperature lower than the heat-deterioration-starting temperature of the heat-deteriorative aromatic compound but sufficient to evaporate the falling liquid fraction, to evaporate a portion of the falling liquid fraction in an evaporation amount in kg/hr corresponding to 1 to 15% by weight of the total amount in kg/hr of the liquid fraction introduced into the second reboiler 33, per one pass of the liquid fraction through the second reboiler 33; (G) the resultant evaporated and non-evaporated portions of the liquid fraction are withdrawn from the second reboiler 33 and returned into the second distillation column 30 through a returning inlet thereof located above the level of the liquid fraction accumulated in the bottom portion of the second distillation column; and (H) the returned evaporated portion in the second distillation column heat-exchanges with the recovered liquid fraction fed into the second distillation column 30, to evaporate the alkyl ether of the heat-deteriorative aromatic compound having the lower boiling temperature than that of the heat-deteriorative compound.

(7) The resultant vapor fraction comprising the alkyl ether of the heat-deteriorative aromatic compound having the lower boiling temperature than that of the heat-deteriorative aromatic compound is delivered through the top outlet of the second distillation column 30, while allowing the resultant liquid fraction comprising the heat-deteriorative aromatic compound to be accumulated in the bottom portion of the second distillation column 30. The delivered vapor fraction through the delivery line 35a is cooled by a cooler 35 to convert the vapor fraction to a vapor/liquid mixture. The vapor/liquid mixture is introduced into a vapor/liquid separator 36 to separate the vapor portion and the liquid portion comprising the alkyl ether of the heat-deteriorative aromatic hydroxyl compound, from each other. The separated vapor portion is discharged through a delivery line 39, and the separated liquid portion is recovered through a recovery line 37. Optionally, a portion of the separated liquid portion is returned into the top portion of the second distillation column 30 through a returning line 35b.

(8) a portion of the liquid fraction accumulated in the bottom portion of the second distillation column 30 and comprising the heat-deteriorative aromatic compound is recovered through the bottom outlet of the second distillation column 30 through a recovery line 38. In the above-mentioned embodiment, the liquid fraction recovered from the second distillation column 30 contains, in addition to the heat-deteriorative aromatic hydroxyl compound, at least one organic compound having a higher boiling temperature than that of the heat-deteriorative aromatic compound.

(9) The recovered liquid fraction from the second distillation column 30 is fed into a middle portion of a third distillation column 40 having a top outlet located in a top portion of the third distillation column and a bottom outlet located in a bottom portion of the third distillation column, the bottom outlet being connected, to a third liquid film-falling reboiler 43 having a plurality of heat conductive vertical pipes spaced from each other and arranged in a heating chamber through which a heating medium passes, as shown in FIG. 1, through a feed line 41.

(10) The fed liquid fraction is distilled in the third distillation column 40 to generate a vapor fraction comprising the heat-deteriorative aromatic compound and a liquid fraction comprising the organic compound having the higher boiling temperature than that of the heat-deteriorative aromatic compound, in such a manner that (I) the liquid fraction in the third distillation column 40 is withdrawn through the bottom outlet of the third distillation column 40, a delivery line 42, a liquid transporting means 44 and a liquid line 49 and introduced into the third reboiler 43 to allow the introduced liquid fraction to fall in the form of liquid films along inner surfaces of the vertical pipes of the third reboiler; (J) the falling liquid fraction through the vertical pipes is heated by the heating medium passing through the heating chamber at a temperature lower than the heat-deterioration-starting temperature of the heat-deteriorative aromatic compound but sufficient to evaporate the falling liquid fraction, to evaporate a portion of the falling liquid fraction in an evaporation amount in kg/hr corresponding to 1 to 15% by weight of the total amount in kg/hr of the liquid fraction introduced into the third reboiler, per one pass of the liquid fraction through the third reboiler; (K) the resultant evaporated and non-evaporated portions of the liquid fraction is withdrawn from the third reboiler 43 and returned into the third distillation column 40 through a returning inlet thereof located above the level of the liquid fraction accumulated in the bottom portion of the third distillation column; and (L) the returned evaporated portion in the third distillation column heat-exchanges to the recovered liquid fraction fed into the third distillation column 40, to evaporate the heat-deteriorative aromatic compound.

(11) The resultant vapor fraction containing the heat-deteriorative aromatic compound is recovered through the top outlet of the third distillation column 40, while allowing the resultant liquid fraction comprising the organic compound having higher boiling temperature than that of the heat-deteriorative compound to be accumulated in the bottom portion of the third distillation column 40. The vapor fraction delivered through the delivery line 35a is introduced into a cooler 45 and is converted to a vapor/liquid mixture. The vapor/liquid mixture is introduced into a vapor/liquid separator 46. The separated vapor portion is discharged through a delivery line 49. The separated liquid portion comprising the heat-deteriorative aromatic di- or more hydroxyl compound is recovered through a recovery line 47. Optionally, a portion of the separated liquid portion is returned into the top portion of the third distillation column 40 through a returning line 45b.

(12) A portion of the liquid fraction accumulated in the bottom portion of the third distillation column 40 is discharged through the bottom outlet of the third distillation column 40, through a delivery line 48.

In the above-mentioned embodiment, the alkyl alcohol is recovered as a first vapor fraction in the first distillation apparatus 20a, the alkyl ether of the heat-deteriorative aromatic hydroxyl compound is recovered as a second vapor fraction in the second distillation apparatus 30a and the heat-deteriorative aromatic hydroxyl compound is recovered as a third vapor fraction in the third distillation apparatus 40a.

When the heat-deteriorative compound contained in the liquid mixture is catechol, the falling liquid films formed in the first, second or third reboiler are heated preferably at an average temperature of 120 to 240° C., more preferably 130 to 220° C., still more preferably 140 to 200° C.

Also, when the heat-deteriorative compound is an aromatic di- or more hydroxyl compound, the Reynolds' number (Re) of the falling liquid films formed in the vertical pipes of the first, second or third reboiler is preferably 700 to 10,000, more preferably 2000 to 8,000, still more preferably 3200 to 7000.

In the above-mentioned embodiment of the process of the present invention, the liquid fraction delivered from the bottom portion of the first distillation column comprises a concentrated aromatic di- or more hydroxyl compound or a mixture of a concentrated aromatic di- or more hydroxyl compound with at least one concentrated alkyl ether of the aromatic di- or more hydroxyl compound. Also, the liquid fraction delivered from the bottom portion of the second distillation column comprises a further concentrated aromatic di- or more hydroxyl compound.

In the above-mentioned embodiment, the lower boiling temperature component contained in the liquid mixture to be fed to the first distillation apparatus contains an alkyl alcohol having a boiling temperature of 10 to 150° C., under ambient atmospheric pressure. Preferably, the lower boiling temperature component comprises a mixture of 60 to 100% by weight, more preferably 80 to 100% by weight of a lower alkyl alcohol having 1 to 4 carbon atoms and exhibiting a boiling temperature of 50 to 120° C. under ambient atmospheric pressure with the balance consisting of at least one other organic or inorganic compound having a boiling temperature of −30 to 150° C., more preferably −25 to 145° C. under ambient atmospheric pressure.

The lower alkyl alcohols is preferably selected from those having 1 to 4 carbon atoms, for example, methyl alcohol, ethyl alcohol, n-propyl alcohol, isopropyl alcohol, n-butyl alcohol and isobutyl alcohol. The other organic or inorganic compound can be selected from, for example, water, alkylethers, for example, dimethyl ether and diethylether, keto-aliphatic alcohol compounds, ketones, glycols, aliphatic carboxylic acid esters, aliphatic hydrocarbons, cycloaliphatic hydrocarbons and aromatic hydrocarbons each having a boiling temperature of −30° C. to 150° C. under ambient atmospheric pressure.

In the liquid mixture for the first distillation, procedure (2), the higher boiling temperature component comprises, for example, 30 to 70% by weight, particularly 35 to 65% by weight of an aromatic di-hydroxyl compound such as hydroquinone or catechol and 30 to 70% by weight, particularly 35 to 65% by weight of an alkyl ether of the aromatic dihydroxyl compound such as guaiacol or monoethyl ether of catechol.

The aromatic dihydroxyl compound may be selected from those having a boiling temperature of 160 to 300° C., particularly 180 to 280° C. under ambient atmospheric pressure and a heat deterioration-starting temperature of 200° C. or more, particularly 250° C. or more, for example, hydroquinone, catechol, resorcinol and substituted aromatic dihydroxyl compounds, for example, 2-methyl catechol, 4-methyl catechol, 2-methyl hydroquinone, 2-chlorocatechol, 4-chlorocatechol. Among the above-mentioned compounds, hydroquinone and catechol are particularly suitable for the process of the present invention.

The alkyl ether of the aromatic dihydroxyl compound include monoalkylethers of the aromatic dihydroxyl compounds, for example, guaiacol and catechol monoethyl ether, and dialkylethers of the aromatic dihydroxyl compounds, for example, dimethoxybenzene and diethoxybenzene. Among the above-mentioned compounds, guaiacol and catechol monoethyl ether are suitable for the process of the present invention.

The liquid mixture usable for the first distillation procedure (2) of the process of the present invention preferably comprises 5 to 40% by weight of an aromatic dihydroxyl compound, 10 to 50% by weight of an alkyl ether of the aromatic dihydroxyl compound and 10 to 50% by weight of a lower alkyl alcohol.

The above-mentioned liquid mixture for the first distillation procedure (2) may be a reaction liquid obtained by an etherification reaction of a lower alkyl alcohol, for example, methyl alcohol or ethyl alcohol with an aromatic dihydroxyl compound, for example, hydroquinone or catechol in the presence of a certain catalyst in a gas phase and containing a resultant monoalkylether of the aromatic dihydroxyl compound, for example, guaiacol or catechol monoethylether.

The reaction liquid comprises a non-reacted lower alkyl alcohol, for example, methyl alcohol or ethyl alcohol, non-reacted aromatic dihydroxyl compound, for example, hydroquinone or catechol, a target reaction product, namely a monoalkylether of the aromatic dihydroxyl compound, for example, guaiacol or catechol monoethyl ether and by-products including dialkylether of the aromatic dihydroxyl compound, for example, dimethoxybenzene or diethoxybenzene, dialkyl ether, for example, dimethylether or diethylether, and a small amount of water. The above-mentioned compounds can be separated from each other and recovered by the process of the present invention.

In the process of the present invention, the distillation procedure (2), (6) or (10) can be effected under ambient atmospheric pressure, a reduced pressure or an increased pressure. Particularly, the first distillation procedure (2) is preferably carried out under a pressure of 1.01 to 2.0 atmospheres, more particularly 1.05 to 1.5 atmospheres. When the first distillation procedure is carried out under the above-mentioned increased pressure, even when the first distillation column is broken by corrosion, the increased inner pressure of the first distillation apparatus can prevent the penetration of air including oxygen gas into the distillation system and thus an ignition of ignitable compounds, for example, dialkyl ether contained in the fed liquid mixture can be prevented and an explosion of the distillation apparatus can be prevented.

The aromatic dihydroxyl compound, for example, catechol has a high heat-deteriorative property and thus when the compound is refined and recovered by a conventional distillation procedure, the compound is deteriorated by heat-decomposition, heat-polymerization or heat-modification, to a great extent, by the heating procedure in the reboiler. In a certain case, by the heat-deterioration of the aromatic dihydroxyl compound, scale is formed on the inner surfaces of the vertical pipes of the reboiler, the heating efficiency of the vertical pipes is greatly decreased, and the falling of the liquid fraction through the vertical pipes is stopped. Therefore, the distillation procedure cannot be continuously carried out over a long period.

However, by the process of the present invention, the above-mentioned problem can be completely solved and the refining procedure of the heat-deteriorative compound can be industrially continued with a high stability over a long period.

EXAMPLES

The process of the present invention will be further explained by the following examples.

Example 1

A multi-component liquid mixture was prepared by an etherification reaction of catechol with methyl alcohol and a removal of a more volatile component from the reaction product mixture by distillation. The resultant crude reaction product mixture, namely the multi-component liquid mixture comprises 50.1% by weight of catechol, 47.0% by weight of guaiacol, and 2.9% by weight of other compounds (for example, heavy-duty compounds), and is fed in the state of a melt into the distillation apparatus as shown in FIG. 1 at a feed rate of 583 kg/hr. In the feeding procedure, catechol was fed at a feed rate of 290.0 kg/hr, guaiacol at a feed rate of 272.0 kg/hr and the other compounds at a feed rate of 16.5 kg/hr.

The distillation of the liquid mixture was continuously carried out under the conditions shown in Table 1 for 40 days. A target refined guaiacol was obtained, as a vapor fraction, in a recovery rate of 283 kg/hr. Also, the liquid fraction, by the distillation, was recovered at a recovery rate of 300 kg/hr. In the recovered liquid fraction, catechol was recovered at a recovery rate of 272 kg/hr, guaiacol at a recovery rate of 7 kg/hr, the other compound at a recovery rate of 16.5 kg/hr and a heat-deterioration product at a recovery rate of 4.6 kg/hr.

In the distillation apparatus, the distillation column was a packed column type of distillation column packed with a regular packing material and had a diameter of column of 900 mm. The reboiler was of a liquid film-falling type. In the liquid film-falling reboiler, the vertical heat-conductive pipes had an inner diameter of 21.6 mm and a length of 1500 mm and numbered 62 pipes.

When the liquid fraction was circulated through the liquid film-falling reboiler, the flow rate of the circulating liquid per unit width of the heat-conductive area of the reboiler was 6865 kg/m.hr. In this example, the falling liquid films had a Reynolds' number (Re) of 5085, determined from the above-mentioned data.

In the principal conditions of the distillation procedures using the distillation column and the liquid film-falling reboiler, the circulating rate of the liquid fraction through the liquid film-falling reboiler was 26 $m^3$/hr, the evaporation amount of the circulating liquid was 4% by weight, based on the total amount of the circulating liquid, and the solution viscosity of the circulating liquid fraction was 1.5 cps (5.4 kg/m·hr).

The distillation conditions and results are shown in Table 1.

TABLE 1

|  | Multi-component liquid mixture fed into distillation column | Vapor fraction delivered from top portion of distillation column | High boiling temperature liquid fraction delivered from bottom portion of distillation column |
|---|---|---|---|
| Flow rate (kg/hr) | 583 | 283 | 300 |
| Composition (kg/hr) |  |  |  |
| Guaiacol | 290.0 | 283 | 7 |
| Catechol | 272.0 | — | 272 |
| Others | 16.5 | — | 16.5 |
| Heat-deterioration product | 4.4 | — | 4.6 |
| Distillation conditions |  |  |  |
| Temperature (° C.) | — | 110 | 155 |
| Heating medium temperature (° C.) | 275 | — | — |
| Pressure (Torr) | — | 30 | — |

Table 1 shows that in the refining process of the present invention for the heat-deteriorative compound (catechol), the heat-deterioration of catechol during the distillation procedure could be restricted to 0.1% by weight or less. Therefore, the target refined guaiacol could be recovered from the reaction product mixture with high stability over a long period, while preventing the heat-deterioration of the non-reacted heat-deteriorative catechol contained in the mixture.

Comparative Example 1

The same multi-component liquid mixture as in Example was subjected to the same distillation procedures as in Example 1, except that the liquid film-falling reboiler was replaced by a conventional forced circulation type reboiler.

As a result, it was found that catechol was heat-deteriorated in an amount of about 7% by weight, and the heat-deterioration product blocked the heat conductive pipes and other conduits in the reboiler, and was accumulated in devices, for example, a transit tank, arranged in the circulating line. Therefore, it was necessary to often stop the distillation procedures for the purpose of cleaning the reboiler and the circulating line and devices. Generally, continuous operation period of the distillation procedures was limited to about two days.

As mentioned above, the conventional distillation procedures applied to the heat-deteriorative compound (catechol)-containing liquid mixture, causes the heat-deteriorative compound to be heat-deteriorated in a high rate, and the distillation yield of the target product to significantly decrease, and thus a great industrial disadvantage to occur.

Example 2

A catechol-containing liquid mixture was subjected to a continuous distillation for 40 days or more by using the distillation system shown in FIG. 3 comprising a first distillation apparatus 20a, a second distillation apparatus 30a and a third distillation apparatus 40a connected successively in series.

The catechol-containing liquid mixture, which had an average temperature of 55° C. and comprised, in an average composition, 290 parts by weight of guaiacol, 274 parts by weight of catechol, 362 parts by weight of methyl alcohol, 47 parts by weight of water and 41 parts by weight of others, was fed in an average feed rate of 1014 kg/hr into the first distillation apparatus 20a including a first distillation column 20 (having a column diameter of 700 mm and an inner pressure of 1.50 kg/cm abs) and a first liquid film-falling reboiler 23 (which had 145 vertical heat-conductive pipes each having an inner diameter of 21.4 mm). The first distillation apparatus 20a was operated under the conditions shown in Table 2.

In the first distillation column 20, a vapor fraction comprising methyl alcohol and a liquid fraction comprising guaiacol and catechol are generated from the fed liquid mixture, and the liquid fraction was accumulated in a bottom portion of the first distillation column 20, circulated through a delivery line 22, a liquid-transporting line 24, a liquid line 29 and a first liquid film-falling reboiler 23 and returned into the bottom portion of the first distillation column 20 at a location close to and above the level of the accumulated liquid fraction in the bottom portion, through a returning line 23a. In the first reboiler, the liquid fraction fell in the form of liquid films along the inner surfaces of a plurality of vertical heat-conductive pipes, while being heated by a heating medium under the conditions shown in Table 2 to evaporate a portion of the falling liquid films in an evaporation amount of 1.4% by weight based on the total amount of the liquid fraction, per pass through the first reboiler. The evaporation temperature was 242° C. on average. The resultant mixture of evaporated portion and non-evaporated portion was returned into the bottom portion of the first distillation column 20. The returned evaporated vapor portion exchanged heat with the liquid mixture fed into the first distillation column 20 to evaporate the lower boiling temperature component comprising methyl alcohol. The resultant vapor fraction flowed upward through and was fractionated in a fractionating device as shown in FIG. 1. The fractionated vapor fraction was delivered from the top portion of the first distillation column 20 through a delivery line 25a. The delivered vapor fraction was cooled by a cooler 25 to condense the vapor fraction. The condensed fraction was introduced into a liquid/vapor separator 26. A non-condensed vapor portion was discharged from the separator 26 through a discharge line 29. The condensed fraction was recovered from the separator 26 through a recovery line 27. Optionally, a portion of the condensed fraction was returned into the top portion of the first distillation column 20. The delivered vapor fraction had an average temperature of 84° C. and comprised, in an average composition, 2 parts by weight of guaiacol; 0 part by weight of catechol, 36.2 parts by weight of methyl alcohol, 47 parts by weight of water and 22 parts by weight of others and delivered at a flow rate of 433 kg/hr.

Also, the liquid fraction containing concentrated catechol and guaiacol had a temperature of 242° C. and comprised, in an average composition, 288 parts by weight of guaiacol, 272 parts by weight of catechol and 21 parts by weight of others. A portion of the liquid fraction was recovered at an average flow rate of 581 kg/hr from the bottom portion of the first distillation column 20 through the liquid-transporting means 24 and a recovery line 28.

The liquid fraction delivered from the bottom portion of the first distillation column 20 and having the above-mentioned average temperature and composition was fed into a middle portion of the second distillation apparatus 30a including a second distillation column 30 having a column diameter of 900 mm and an inner pressure of 0.04 kg/cm$^2$ abs and a second liquid film-falling reboiler 33 having 62 vertical heat-conductive pipes each having an inner diameter of 21.4 mm. The second distillation apparatus 30a was operated under the conditions shown in Table 2.

In the second distillation column 30, a vapor fraction comprising guaiacol and a liquid fraction comprising catechol were generated from the fed liquid fraction.

The liquid fraction was accumulated in a bottom portion of the second distillation column 30, circulated through a delivery line 33, a liquid-transporting line 34, a liquid line 39 and a second liquid film-falling reboiler 33, and then returned into the bottom portion of the second distillation column 30 at a location close to and above the level of the accumulated liquid fraction in the bottom portion, through a returning line 33a.

In the second reboiler, the liquid fraction fell in the form of liquid films along the inner surfaces of a plurality of vertical heat-conductive pipes, while being heated by a heating medium under the conditions shown in Table 2 to evaporate a portion of the falling liquid films in an evaporation amount of 4.0% by weight based on the total amount of the liquid fraction, per pass through the second reboiler. The evaporation temperature was 155° C. on average. The resultant mixture of the evaporated portion and the non-evaporated portion was returned into the bottom portion of the second distillation column 30. The returned evaporated vapor portion exchanged a heat over thereby to the liquid mixture fed into the second distillation column 30 to evaporate the lower boiling temperature component comprising guaiacol. The resultant vapor fraction flowed upward through, and was fractionated in, a fractionating section as shown in FIG. 1. The fractionated vapor fraction was delivered from the top portion of the second distillation column 30 through a delivery line 35a. The delivered vapor fraction was cooled by a cooler 35 to condense the vapor fraction. The condensed fraction was introduced into a liquid/vapor separator 36. A non-condensed vapor portion was discharged from the separator 36 through a discharge line 39. The condensed fraction was recovered from the separator 36 through a recovery line 37. Optionally a portion of the condensed fraction was returned into the top portion of the second distillation column 30. The delivered vapor fraction had an average temperature of 110° C. and comprised, in an average composition, 283 parts by weight of guaiacol, 0 part by weight of catechol, 0 part by weight of methyl alcohol, 0 part by weight of water and 0 part by weight of others, and was delivered at a flow rate of 283 kg/hr.

Also, the liquid fraction containing concentrated catechol had an average temperature of 155° C. and comprised, in an average composition, 5 parts by weight of guaiacol, 272 parts by weight of catechol and 21 parts by weight of others. A portion of the liquid fraction was recovered at an average flow rate of 298 kg/hr from the bottom portion of the second distillation column 30 through the liquid-transporting means 34 and a recovery line 38.

The liquid fraction delivered from the bottom portion of the second distillation column 30 and having the above-mentioned average temperature and composition was fed into a middle portion of the third distillation apparatus 40a including a third distillation column 40 having a column diameter of 600 mm and an inner pressure of 0.04 kg/cm abs and a third liquid film-falling reboiler 43 having 64 vertical heat-conductive pipes each having an inner diameter of 21.4 mm.

The third distillation apparatus 40a was operated under the conditions shown in Table 2.

In the third distillation column 40, a vapor fraction comprising catechol and a liquid fraction having organic compounds having a higher boiling temperature than that of catechol, were generated from the fed liquid mixture. The liquid fraction was accumulated in a bottom portion of the third distillation column 40, circulated through a delivery line 42, a liquid-transporting line 44, a liquid line 49 and a third liquid film-falling reboiler 43 and returned into the bottom portion of the third distillation column 40 at a location close to and above the level of the accumulated liquid fraction in the bottom portion, through a returning line 43a.

In the third reboiler 43, the liquid fraction fell in the form of liquid films along the inner surfaces of a plurality of vertical heat-conductive pipes, while being heated by a heating medium under the conditions shown in Table 2 to evaporate a portion of the falling liquid films in an evaporation amount of 1.4% by weight based on the total amount of the liquid fraction, per pass through the first reboiler. The evaporation temperature was 188° C. on average. The resultant mixture of evaporated portion and non-evaporated portion was returned into the bottom portion of the third distillation column 40. The returned evaporated vapor portion exchanged heat with the liquid mixture fed into the third distillation column 40 to evaporate the lower boiling temperature component comprising catechol. The resultant vapor fraction flowed upward through, and fractionated in, a fractionating section as shown in FIG. 1. The fractionated vapor fraction was delivered from the top portion of the third distillation column 40 through a delivery line 45a. The delivered vapor fraction was cooled by a cooler 45 to condense the vapor fraction. The condensed fraction was introduced into a liquid/vapor separator 46. A non-condensed vapor portion was discharged from the separator 46 through a discharge line 49. The condensed fraction was recovered from the separator 46 through a recovery line 47. Optionally a portion of the condensed fraction was returned into the top portion of the third distillation column 40. The delivered vapor fraction containing, as a principal component, catechol had an average temperature of 137° C. and comprised, in an average composition, 5.0 parts by weight of guaiacol, 270.8 parts by weight of catechol, 0 part by weight of methyl alcohol, 0 part by weight of water and 16.5 parts by weight of others and delivered at an average flow rate of 292.3 kg/hr.

Also, the liquid fraction containing concentrated higher boiling temperature compounds had an average temperature of 188° C. and comprised, in an average composition, 0 part by weight of guaiacol, 1.1 parts by weight of catechol and 4.8 parts by weight of others. A portion of the liquid fraction was recovered at an average flow rate of 5.9 kg/hr from the bottom portion of the third distillation column 40 through the liquid-transporting means 44 and a recovery line 48.

The catechol-containing liquid mixture fed into the first distillation column 20 at a feed rate of 1014 kg/hr contained a heat-deterioration product of catechol in an amount of 3.1 kg/hr which corresponded to 1.13% by weight based on the amount of catechol fed into the first distillation column 20, namely 274 kg/hr, and the liquid fraction delivered from the first distillation column 20 contained the heat-deterioration product of catechol in an amount of 4.4 kg/hr which corresponded to 1.61% by weight based on the amount of catechol fed into the first distillation column 20, namely, 274 kg/hr.

Also, the liquid fraction recovered from the bottom portion of the second distillation column 30 contained the heat-deterioration product of catechol in an amount of 4.6 kg/hr which corresponded to 1.68% by weight based on the amount of catechol fed into the first distillation column 20, namely 274 kg/hr.

Further, the liquid fraction recovered from the bottom portion of the third distillation column 40 contained the heat-deterioration product of catechol in an amount of 4.8 kg/hr which corresponded to 1.75% by weight based on the amount of catechol fed into the first distillation column 20, namely 274 kg/hr.

Accordingly, the increase in content in % by weight of the heat-deterioration product of catechol during the distillation procedures in the first, second and third distillation apparatuses was 0.62% by weight which was surprisingly low.

In this example, it was confirmed that the distillation procedures could be continuously carried out for at most 250 days, without a need of cleaning of the first, second and third reboilers 23, 33 and 43, which need of the cleaning caused the distillation procedures to be stopped.

The constitutions and operational conditions of the first, second and third distillation columns and reboilers and the contents of the heat deterioration product of catechol in the liquid fractions delivered from the first, second and third distillation columns are shown in Table 2.

TABLE 2

| | First distillation apparatus | Second distillation apparatus | Third distillation apparatus |
|---|---|---|---|
| Distillation column | | | |
| Type | Packed column type | Packed column type | Packed column type |
| Inner diameter (mm) | 700 | 900 | 600 |
| Height (mm) | 9,500 | 20,000 | 12,000 |
| Reboiler | | | |
| Type | Liquid film-falling type | Liquid film-falling type | Liquid film-falling type |
| Heat-conductive pipes | | | |
| Inner diameter (mm) | 21.4 | 21.4 | 21.4 |
| Length (mm) | 3,000 | 1,500 | 1,000 |
| The number | 145 | 62 | 64 |

TABLE 2-continued

|  | First distillation apparatus | Second distillation apparatus | Third distillation apparatus |
|---|---|---|---|
| Operational conditions for liquid fraction |  |  |  |
| Circulating rate (kg/hr) | 48,600 | 28,600 | 19,600 |
| Evaporation amount (% by wt) | 1.4 | 4.0 | 13.0 |
| Viscosity (kg/m · hr) | 2.6 | 5.4 | 3.2 |
| Flow rate per unit width of heat-conductive area (kg/m · hr) | 4,990 | 6,870 | 4,560 |
| Raynold's number | 7,690 | 5,085 | 5,760 |
| Content of catechol heat-deterioration product (% by wt) (*)$_1$ | 1.61 | 1.68 | 1.75 |

Note:
(*)$_1$ The content of catechol heat-deterioration product based on the amount of catechol contained in the liquid mixture fed to the first distillation column was 1.13% by weight.

Comparative Example 2

The same distillation procedures as in Example 2 were applied to the same liquid mixture as in Example 2, except that each of the first, second and third liquid film-falling reboilers was replaced by a conventional forced circulation reboiler.

After the distillation procedures were continuously carried out for more than 40 days, it was found that the catechol fed into the first distillation apparatus was heat-deteriorated in an amount of 30% by weight or more by the first distillation therein, and in each of the second and third distillation apparatuses, catechol was heat-deteriorated in an amount of 4.9% by weight based on the original amount of catechol fed into the first distillation column. Therefore, as a whole, the recovery of catechol was low.

Also, the heat-deterioration product of catechol caused the heat-conductive pipes and the circulation lines to be blocked and/or was accumulated in the transit tanks and distillation columns. Therefore, the distillation procedures had to be stopped often (every two days), because the distillation apparatuses had to be cleaned.

Further, in the distillation procedures of Comparative Example 2, catechol contained in the liquid mixture fed into the first distillation column was heat-deteriorated in a total amount of about 40% by weight, and thus a serious economical disadvantage occurred.

In the process of the present invention wherein a liquid film-falling reboiler is used in combination with a distillation column, the heat-deteriorative compound-containing liquid mixture is fed into a distillation column and the resultant liquid fraction containing the heat-deteriorative compound is subjected to an evaporation procedure under specific conditions, in the liquid film-falling reboiler.

Namely, the evaporation procedure is applied to the liquid fraction in the form of liquid films falling along the inner surfaces of the vertical pipes at a temperature lower than the heat-deterioration-starting temperature of the heat-deteriorative compound and sufficient to evaporate the liquid fraction to such an extent that the liquid fraction evaporated in an amount corresponding to 1 to 15% by weight of the total amount of the liquid fraction introduced into the reboiler, per pass through the reboiler. Under the above-mentioned specific conditions, the heat-deterioration of the heat-deteriorative compound can be prevented or restricted, and the breakage of the falling liquid films of the liquid fraction in the reboiler can be prevented or reduced. The prevention or reduction of the breakage of the falling liquid films contributes to preventing local heating of the heat-deteriorative compound at a high temperature and thus the heat-deterioration of the heat-deteriorative compound can be prevented or reduced.

Accordingly, in the process of the present invention, the lower boiling temperature component can be recovered as a vapor fraction, and the higher boiling temperature component can be recovered as a liquid fraction with a high stability, while preventing or reducing the heat-deterioration of the heat-deteriorative compound. Also, the distillation procedures can be continuously carried out over a long period.

The process of the present invention can be applied to a liquid mixture containing a heat-deteriorative aromatic hydroxyl compound, a lower alkyl alcohol and a etherification reaction product of the aromatic hydroxyl compound with the lower alkyl alcohol. By the process of the present invention, the aromatic hydroxyl compound can be protected from heat-deterioration and recovered in a high yield, and each of the lower alkyl alcohol and the etherification reaction product can be collected in a high yield.

What is claimed is:

1. A process for refining a heat-sensitive compound contained in a multi-component liquid mixture by distillation, comprising the steps of:

(1) feeding a multi-component liquid mixture comprising a lower boiling temperature component and a higher boiling temperature component containing a heat-sensitive component, into a distillation column having a top outlet located in a top portion of the distillation column and a bottom outlet located in a bottom portion of the distillation column, the bottom outlet being connected to a falling-film reboiler having a plurality of heat-conductive vertical pipes spaced from each other and arranged in a heating chamber through which a heating medium passes;

(2) distilling the multi-component liquid mixture in the distillation column to generate a vapor fraction comprising the lower boiling temperature component and a liquid fraction comprising the higher boiling temperature component, in such a manner that (A) the liquid fraction is withdrawn through the bottom outlet of the distillation column and introduced into the reboiler at a rate such that the introduced liquid fraction falls in the form of a film along inner surfaces of the vertical pipes at a Reynolds number (Re) of 700 to 10,000; (B) the film falling through the vertical pipes is heated by the heating medium passing through the heating chamber to a temperature lower than the heat-deterioration-starting temperature of the heat-sensitive compound but sufficient to evaporate a portion of the falling film liquid fraction wherein an evaporation rate of the falling film is controlled at 1% to 15% by weight of the flow rate of the liquid fraction introduced into the reboiler, per one pass of the liquid fraction through the reboiler; (C) the resultant evaporated and non-evaporated portions of the liquid fraction are withdrawn from the reboiler and returned into the distillation column through a returning inlet thereof located above the level of the liquid fraction accumulated in the bottom portion of the distillation column; and (D) the evaporated portion of the returned liquid fraction heat exchanges with the multi-component liquid mixture fed into the distillation column to evaporate the lower boiling temperature component;

(3) delivering the resultant vapor fraction comprising the lower boiling temperature component through the top outlet of the distillation column while allowing the resultant liquid fraction comprising the higher boiling temperature component to be accumulated in the bottom portion of the distillation column; and (4) recovering a portion of the liquid fraction accumulated in the bottom portion of the distillation column and comprising the higher boiling temperature component containing the heat-sensitive compound from the bottom portion of the distillation column.

2. The process for refining a heat-deteriorative compound as claimed in claim 1, wherein the multi-component liquid mixture contains the heat-deteriorative compound in an amount of 5% by weight or more, based on the total weight of the multi-component liquid mixture.

3. The process for refining a heat-deteriorative compound as claimed in claim 1, wherein the heat-deteriorative compound has a boiling temperature of 100 to 400° C. under ambient atmospheric pressure, a freezing temperature of −10° C. to 300° C. and a heat-deterioration-starting temperature of 150 to 400° C.

4. The process for refining a heat-sensitive compound as claimed in claim 1, wherein the heat-sensitive compound comprises at least one member selected from the group consisting of aromatic compounds having at least one hydroxyl group, esters of aliphatic polycarboxylic acids with aromatic hydroxyl compounds and esters of aromatic polycarboxylic acids with alkyl alcohols.

5. The process for refining a heat-deteriorative compound as claimed in claim 4, wherein the heat-deteriorative aromatic compounds having one or more hydroxyl groups are selected from the group consisting of phenol, guaiacol, catechol, hydroquinone, resorcinol, 2-methyl catechol, 4-methyl catechol, 2-methyl hydroquinone, 2-chlorocatechol, and 4-chloro catechol, the esters of aliphatic polycarboxylic acids with aromatic hydroxyl compounds are selected from the group consisting of diphenyl malonate, diphenyl oxalate and diphenyl carbonate, and the esters of aromatic polycarboxylic acids with alkyl alcohols are selected from the group consisting of alkyl esters of biphenyl-tetracarboxylic acid and tetraalkyl esters of pyromellitic acid.

6. The process for refining a heat-deteriorative compound as claimed in claim 1, wherein the higher boiling temperature component contains, in addition to the heat-deteriorative compound, a heat-resistive organic compound having a boiling temperature of 100 to 400° C. under ambient atmospheric pressure.

7. The process for refining a heat-deteriorative compound as claimed in claim 1, wherein the lower boiling temperature component comprises at least one organic compound having a boiling temperatures of 50 to 200° C. below the boiling temperature of the organic compounds contained in the higher boiling temperature component under ambient atmospheric pressure.

8. The process for refining a heat-deteriorative compound as claimed in claim 1, wherein the multi-component liquid mixture contains a heat-deteriorative aromatic compound having one or more hydroxyl groups and exhibiting a boiling temperature of 150 to 350° C. under ambient atmospheric pressure, in an amount of 50% by weight or more, and at least one other organic compound soluble or compatible with the heat-deteriorative compound at a temperature of 100 to 300° C.

9. The process for refining a heat-deteriorative compound as claimed in claim 1, wherein the liquid films of the liquid fraction falling along the inner surfaces of the vertical pipes of the reboiler have an average thickness of 0.1 to 5 mm.

10. The process for refining a heat-sensitive compound as claimed in claim 1, further comprising, when the higher boiling temperature component contained in the liquid fraction recovered in the recovery step (4) contains, in addition to the heat-sensitive compound, at least one organic compound having a boiling temperature lower than that of the heat-sensitive compound, the steps of:

(5) feeding the recovered liquid fraction into an additional distillation column having a top outlet located in a top portion of the additional distillation column and a bottom outlet located at a bottom portion of the additional distillation column, the bottom outlet being connected to an additional liquid falling film reboiler having a plurality of heat-conductive vertical pipes spaced from each other and arranged in a heating chamber through which a heating medium passes;

(6) distilling the fed liquid fraction in the additional distillation column to generate a liquid fraction comprising the heat-sensitive compound and a vapor fraction comprising the organic compound having a lower boiling temperature than that of the heat-sensitive compound, in such a manner that (E) the liquid fraction is withdrawn through the bottom outlet of the additional distillation column and introduced into the additional reboiler at a rate such that the introduced liquid fraction falls in the form of a film along inner surfaces of the vertical pipes of the additional reboiler at a Reynolds number (Re) of from 700 to 10,000; (F) the falling liquid film being heated by the heating medium passing through the heating chamber to a temperature lower than the heat-deterioration-starting temperature of the heat-sensitive compound but sufficient to evaporate a portion of the falling film liquid fraction wherein an evaporation rate of the falling film is controlled at 1% to 15% by weight of the flow of the liquid fraction introduced into the additional reboiler, per one pass of the liquid fraction through the additional reboiler; (G) the resultant evaporated and non-evaporated portions of the liquid fraction being withdrawn from the additional reboiler and returned into the additional distillation column through a returning inlet thereof located above the level of the liquid fraction accumulated in the bottom portion of the additional distillation column; and (H) the returned evaporated portion in the additional distillation column heat-exchanges with the recovered liquid fraction being fed into the additional distillation column, to evaporate the organic compound having the lower boiling temperature than that of the heat-sensitive compound;

(7) delivering the resultant vapor fraction comprising the organic compound having a lower boiling temperature than that of the heat-sensitive compound through the top outlet of the additional distillation column, while allowing the resultant liquid fraction comprising the heat-sensitive compound to be accumulated in the bottom portion of the additional distillation column; and (8) recovering a portion of the liquid fraction accumulated in the bottom portion of the additional distillation column and comprising the heat-sensitive compound through the bottom portion of the additional distillation column and comprising the heat-sensitive compound through the bottom outlet of the additional distillation column.

11. The process for refining a heat-sensitive compound as claimed in claim 10, further comprising; when the liquid fraction recovered from the additional distillation column in step (8) contains, in addition to the heat-sensitive compound, at least one organic compound having a higher boiling temperature than that of the heat-sensitive compound, the steps of:

(9) feeding the recovered liquid fraction from the additional distillation column into a further additional distillation column having a top outlet located in a top portion of the further additional distillation column and a bottom outlet located in a bottom portion of the further additional distillation column, the bottom outlet being connected to a further additional falling film reboiler having a plurality of heat-conductive vertical pipes spaced from each other and arranged in a heating chamber through which a heating medium passes;

(10) distilling the fed liquid fraction in the further additional distillation column to generate a vapor fraction comprising the heat-sensitive compound and a liquid fraction comprising the organic compound having the higher boiling temperature than that of the heat-sensitive compound, in such a manner that (I) the liquid fraction in the further additional distillation column is withdrawn through the bottom outlet of the further additional distillation column and introduced into the further additional falling film reboiler at a rate such that the introduced liquid fraction falls in the form of a film along inner surfaces of the vertical pipes of the further additional reboiler at a Reynolds number (Re) of from 700 to 10,000; (J) the falling film liquid fraction being heated by the heating medium passing through the heating chamber to a temperature lower than the heat-deterioration-starting temperature of the heat-sensitive compound but sufficient to evaporate a portion of the falling film liquid fraction wherein an evaporation rate of the falling film is controlled at 1% to 15% by weight of the flow of the liquid fraction introduced in to the further additional reboiler, per one pass of the liquid fraction through the further additional reboiler; (K) the resultant evaporated and non-evaporated portions of the liquid fraction being withdrawn from the further additional reboiler and returned into the further additional distillation column through a returning inlet thereof located above the level of the liquid fraction accumulated in the bottom portion of the further additional distillation column; and (L) the returned evaporated portion in the further additional distillation column being heat-exchanged with the recovered liquid fraction fed to the further additional distillation column, to evaporate the heat-sensitive compound

(11) recovering the resultant vapor containing the heat-sensitive compound through the top outlet of the further additional distillation column, while allowing the resultant liquid fraction comprising the organic compound having a higher boiling temperature than that of the heat-sensitive compound to be accumulated in the bottom portion of the further additional distillation column; and

(12) discharging a portion of the liquid fraction accumulated in the bottom portion through the bottom outlet of the further additional distillation column.

12. The process for refining a heat-sensitive compound as claimed in claim 1, wherein (1) a multi-component liquid mixture comprises a lower boiling temperature component comprising at least one alkyl alcohol having 1 to 20 carbon atoms and a higher boiling temperature component comprising a heat-sensitive aromatic compound having at least two hydroxyl groups and an alkyl ether of the aromatic compound having at least two hydroxyl groups, is fed into a first distillation column having a top outlet located in a top portion of the first distillation column and a bottom outlet located at a bottom portion of the first distillation column, the bottom outlet being connected to a first falling film reboiler having a plurality of heat-conductive vertical pipes spaced from each other and arranged in a heating chamber through which a heating medium passes;

(2) the fed multi-component liquid mixture is then distilled in the first distillation column to generate a vapor fraction comprising the lower boiling temperature component and a liquid fraction comprising the higher boiling temperature component, in such a manner that (A) the liquid fraction is withdrawn through the bottom outlet of the first distillation column and introduced in the first reboiler at a rate such that the introduced liquid fraction falls in the form of a film along the inner surfaces of the vertical pipes at a Reynolds number (Re) of 700 to 10,000; (B) the falling film liquid fraction is heated by the heating medium passing through the heating chamber at a temperature lower than the heat deterioration-starting temperature of the aromatic compound having at least two hydroxyl groups and sufficient to evaporate a portion of the falling film liquid fraction wherein an evaporation rate of the falling film is controlled at 1% to 15% by weight of the flow of the liquid fraction introduced into the first reboiler, per one pass of the liquid fraction through the first reboiler; (C) the resultant evaporated and non-evaporated portions of the liquid fraction are withdrawn from the first reboiler and returned into the first distillation column through a returning inlet thereof located above the level of the liquid fraction accumulated in the bottom portion of the first distillation column; and (D) the evaporated portion of the returned liquid fraction heat-exchanges with the multi-component liquid mixture fed into the first distillation column to evaporate the lower boiling temperature component;

(3) the resultant vapor fraction comprising the lower boiling temperature component is delivered through the top outlet of the first distillation column, while allowing the resultant liquid fraction comprising the higher boiling temperature component to accumulate in the bottom portion of the first distillation column;

(4) a portion of the liquid fraction accumulated in the bottom portion of the first distillation column and comprising the higher boiling temperature component containing the heat-sensitive aromatic compound having at least two hydroxyl groups is recovered through the bottom outlet of the first distillation column;

(5) the recovered liquid fraction, which comprises the higher boiling temperature component comprising the heat-sensitive aromatic compound having at least two hydroxyl groups and the alkyl ether of the heat-sensitive aromatic compound having a boiling temperature lower than that of the heat-sensitive compound, is fed into a second distillation column having a top outlet located in a top portion of the second distillation column and a bottom outlet located in a bottom portion of the second distillation column, the bottom outlet being connected to a second liquid falling film reboiler having a plurality of heat-conductive vertical pipes spaced from each other and arranged in a heating chamber through which a heating medium passes;

(6) the fed liquid fraction is distilled in the second distillation column to generate a liquid fraction comprising the heat-sensitive aromatic compound and a vapor fraction comprising the alkyl ether of the heat-sensitive aromatic compound having a lower boiling temperature than that of the heat-sensitive aromatic compound, in such a manner that (E) the liquid fraction in the second distillation column is withdrawn through the bottom outlet of the second distillation column and introduced into the second reboiler at a rate such that the introduced liquid fraction falls in the form of a liquid film along inner surfaces of the vertical pipes of the second reboiler at a Reynolds number (Re) of 700 to 10,000; (F) the falling film liquid fraction is heated by the heating medium passing through the heating chamber to a temperature lower than the heat deterioration- starting temperature of the heat-sensitive aromatic compound and sufficient to evaporate a portion of the falling film liquid fraction wherein an evaporation rate of the falling film is controlled at 1% to 15% by weight of the flows of the liquid fraction introduced into the second reboiler, per one pass of the liquid fraction through the second reboiler; (G) the resultant evaporated and non-evaporated portions of the liquid fraction are withdrawn from the second reboiler and returned to the second distillation column through a returning inlet thereof located above the level of the liquid fraction accumulated in the bottom potion of the second distillation column; and (H) the returned evaporated potion in the second distillation column heat-exchanges with the recovered liquid fraction fed into the second distillation column, to evaporate the alkyl ether of the heat-sensitive aromatic compound having the lower boiling temperature than that of the heat-sensitive compound;

(7) the resultant vapor fraction comprising the alkyl ether of the heat-sensitive aromatic compound having the lower boiling temperature than that of the heat-sensitive aromatic compound is delivered through the top outlet of the second distillation column, while allowing the resultant liquid fraction comprising the heat-sensitive compound to be accumulated in the bottom portion of the second distillation column 1; and (8) a portion of the liquid fraction accumulated in the bottom portion of the second distillation column and comprising the heat-sensitive aromatic compound is recovered through the bottom outlet of the second distillation column.

13. The process for refining a heat-sensitive compound as claimed in claim 12, wherein the liquid fraction recovered from the second distillation column contains, in addition to the heat-sensitive aromatic compound, at least one organic compound having a higher boiling temperature than that of the heat-sensitive compound, (9) the recovered liquid fraction from the second distillation column is fed into a third distillation column having a top outlet located in a top portion of the third distillation column and a bottom outlet located in a bottom portion of the third distillation column, the bottom outlet being connected to a third liquid falling-film reboiler having a plurality of heat-conductive vertical pipes spaced from each other and arranged in a heating chamber through which a heating medium passes;

(10) the fed liquid fraction is distilled in the third distillation column to generate a vapor fraction comprising the heat-sensitive compound and a liquid fraction comprising the organic compound having a higher boiling temperature than that of the heat-sensitive compound, in such a manner that (I) the liquid fraction in the third distillation column is withdrawn through the bottom outlet of the third distillation column and introduced into the third reboiler at a rate such that the introduced liquid fraction falls in the form of a film along inner surfaces of the vertical pipes of the third reboiler at a Reynolds number (Re) of 700 to 10,000; (J) the falling film liquid fraction is heated by the heating medium passing through the heating chamber to a temperature lower than the heat-deterioration-starting temperature of the heat-sensitive compound but sufficient to evaporate a portion of the falling film liquid fraction wherein an evaporation rate of the falling film is controlled at 1 to 15% by weight of the flow of the liquid fraction introduced into the third reboiler, per one pass of the liquid fraction through the third reboiler; (K) the resultant evaporated and non-evaporated portions of the liquid fraction are withdrawn from the third reboiler and returned to the third distillation column through a returning inlet thereof located above the level of the liquid fraction accumulated in the bottom potion of the third distillation column; and (L) the returned evaporated portion in the third distillation column heat-exchanges with the recovered liquid fraction fed into the third distillation column, to evaporate the heat-sensitive compound;

(11) the resultant vapor containing the heat-sensitive compound is recovered through the top outlet of the third column, while allowing the resultant liquid fraction comprising the organic compound having a higher boiling temperature than that of the heat-sensitive compound to be accumulated in the bottom portion of the third distillation column; and

(12) a portion of the liquid fraction accumulated in the bottom portion of the third distillation column is discharged through the bottom outlet of the third distillation column.

14. The process for refining a heat-deteriorative compound as claimed in claim 18, wherein the lower boiling temperature component contained in the multi-component liquid mixture fed into the first distillation column comprises 60 to 100% by weight of alkyl alcohol having 1 to 4 carbon atoms and 0 to 40% by weight of organic compound having a boiling temperature of −30° C. to 150° C. under ambient atmospheric pressure and different from the alkyl alcohol.

15. The process for refining a heat-deteriorative compound as claimed in claim 12, wherein the higher boiling temperature compound contained in the multi-component liquid mixture fed into the first distillation column comprises 30 to 70% by weight of at least one member selected from the group consisting of hydroquinone and catechol and 30 to 70% by weight of at least one member selected from the groups consisting of mono- and di-alkyl ethers of hydroquinone and catechol.

16. The process for refining a heat-deteriorative compound as claimed in claim 12, wherein the multi-component liquid mixture fed into the first distillation column comprises 5 to 40% by weight of an aromatic compound having two hydroxyl groups, 10 to 50% by weight of at least one alkyl alcohol having 1 to 4 carbon atoms, and 10 to 50% by weight of at least one member selected from mono- and di-$c_1$-$c_4$ alkyl ethers of the aromatic compound having two hydroxyl groups.

17. The process for refining a heat-deteriorative compound as claimed in claim 12, wherein the multi-component liquid mixture is a liquid containing etherification reaction products of an alkyl alcohol having 1 to 4 carbon atoms with aromatic compound having two hydroxyl groups, and contains at least one member selected from mono- and di-alkyl ethers of the aromatic compounds having two hydroxyl groups.

18. The process for refining a heat-deteriorative compound as claimed in claim 12, wherein the distilling step in the first distillation column is carried out under a pressure of 1.01 to 2.0 atmospheres.

* * * * *